United States Patent
Tauch et al.

(10) Patent No.: US 6,777,229 B1
(45) Date of Patent: Aug. 17, 2004

(54) **PLASMIDS FROM *CORYNEBACTERIUM GLUTAMICUM* AND USE THEREOF**

(75) Inventors: Andreas Tauch, Bielefeld (DE); Jorn Kalinowski, Bielefeld (DE); Alfred Puhler, Bielefeld (DE); Georg Thierbach, Bielefeld (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/704,725

(22) Filed: Nov. 3, 2000

(30) Foreign Application Priority Data

Nov. 5, 1999 (DE) .......................................... 199 53 206

(51) Int. Cl.[7] .......................... C12N 15/63; C07H 21/04
(52) U.S. Cl. .................... 435/320.1; 435/183; 435/106; 536/23.1; 536/23.2; 536/23.7; 536/24
(58) Field of Search .............................. 435/106, 320.1, 435/183; 536/23.1, 25.2

(56) References Cited

U.S. PATENT DOCUMENTS

| 5,175,108 A | 12/1992 | Bachmann et al. | ..... 435/252.32 |
| 6,107,063 A | 8/2000 | Moeckel et al. | ............ 435/116 |

FOREIGN PATENT DOCUMENTS

| EP | 472 869 | 3/1992 |
| WO | WO 95/19442 | 7/1995 |

OTHER PUBLICATIONS

Zhang et al., Molecular Analysis and Characterization of a Broad–Host–Range Plasmid, pEP–2, Journal of Bacteriology, Vol 176, No. 18, Sep. 1994, pp. 5718–5728.*

Guillouet et al., Expression of the *Escherichia coli* Catabolic Threonine Dehydratase in Corynebacterium glutamicum and Its Effect on Isoleucine Production, Applied and Environmental Microbiology, Vol 65, No. 7, Jul. 1999, pp. 3100–3107.*

Database EMBL Online, accession No. Y14748, Sep. 8, 1997, Nesvera et al., "Corynebacterium glutamicum plasmid pCG4 integron (InCg) sequence," XP002159885.

* cited by examiner

Primary Examiner—Richard Hutson
(74) Attorney, Agent, or Firm—Pillsbury Winthrop LLP

(57) ABSTRACT

This invention relates to the mutually compatible plasmids pTET3 and pCRY4, isolated from the strain of Corynebacterium glutamicum deposited under DSM number 5616, wherein plasmid pTET3 is characterised by 1.1 a length of ~27.8 kbp and the restriction map shown in FIG. 1,
1.2 a replication region comprising the nucleotide sequence shown in SEQ ID no. 1 and
1.3 an antibiotic resistance region consisting of a tetA gene imparting tetracycline resistance and an aadA gene imparting streptomycin and spectinomycin resistance, shown in SEQ ID no. 6, and plasmid pCRY4 is characterised by 1.4 a length of ~48 kbp and the restriction map shown in FIG. 2 and
1.5 a replication region comprising the nucleotide sequence shown in SEQ ID no. 4 to composite plasmid vectors of these plasmids which are capable of autonomous replication in coryneform bacteria and to processes for the production of L-amino acids, vitamins and nucleotides using these bacteria.

14 Claims, 4 Drawing Sheets pTET3-DNA pCRY4-DNA pTET3-DNA

SEQUENCE LISTING

```
<160> NUMBER OF SEQ ID NOS: 10

<210> SEQ ID NO 1
<211> LENGTH: 4539
<212> TYPE: DNA
<213> ORGANISM: Corynebacterium glutamicum
<220> FEATURE:
<221> NAME/KEY: CDS
<222> LOCATION: (228)..(824)
<223> OTHER INFORMATION: parA
<221> NAME/KEY: CDS
<222> LOCATION: (1829)..(3295)
<223> OTHER INFORMATION: repA

<400> SEQUENCE: 1
cctaggctta gatgtgctgt cataattttc gcccctcccg tcagacattt ggacatggat      60
ctcgggaaag attaagcggg ggaacttgaa ataattccac tttaaactag gaaatagcag     120
gtcaaagcga tatgttaagg cgctataaca tgagtatgtt atagcgctaa aacacacaac     180
atacttatgt tatgcagcta agacggaagt atgtcagact gataatc atg tcc ata        236
                                                   Met Ser Ile
                                                     1 ctg act atc gct cac aca aaa ggc ggc gtg gga aaa acg acc tct gca        284
Leu Thr Ile Ala His Thr Lys Gly Gly Val Gly Lys Thr Thr Ser Ala
        5                  10                  15 gtg ctt ttg tgt gca gct gcc cac gcc cgc gga cta gcc gtt acc ctc        332
Val Leu Leu Cys Ala Ala Ala His Ala Arg Gly Leu Ala Val Thr Leu
 20                  25                  30                  35 att gac tcc gac gct cag ggc acc gcc acc gcc tgg gcc cac gct gcc        380
Ile Asp Ser Asp Ala Gln Gly Thr Ala Thr Ala Trp Ala His Ala Ala
                 40                  45                  50 gaa gaa gcc ggt gat act ttc ccg tgg cct atc atc aca gcg gcc acg        428
Glu Glu Ala Gly Asp Thr Phe Pro Trp Pro Ile Ile Thr Ala Ala Thr
```

-continued

```
                55                  60                  65
cct gcc cac ctt gcc cga acg ctc gac ggc cat aac gga ctc gtc atc       476
Pro Ala His Leu Ala Arg Thr Leu Asp Gly His Asn Gly Leu Val Ile
        70                  75                  80 gtt gat acc ccg ccc ggt ggc tac gaa gtg atc gag acc gcc atc gaa       524
Val Asp Thr Pro Pro Gly Gly Tyr Glu Val Ile Glu Thr Ala Ile Glu
    85                  90                  95 gca ggc gac ctc atc ctg atc ccc acc tct gcc tcc ccg cta gac atc       572
Ala Gly Asp Leu Ile Leu Ile Pro Thr Ser Ala Ser Pro Leu Asp Ile
100                 105                 110                 115 aat cga gtc tgg cca act gtt gag gcc acc agt cac aag ccc gcc gta       620
Asn Arg Val Trp Pro Thr Val Glu Ala Thr Ser His Lys Pro Ala Val
                120                 125                 130 gtc tgt cta tcc cag atc gac tcc cgc acc acc ttg ccc aag att gcc       668
Val Cys Leu Ser Gln Ile Asp Ser Arg Thr Thr Leu Pro Lys Ile Ala
            135                 140                 145 cgt acc gca ctt gaa aac gaa ggc gtc gtc gtc gct gaa acg gag atc       716
Arg Thr Ala Leu Glu Asn Glu Gly Val Val Val Ala Glu Thr Glu Ile
        150                 155                 160 ccc gcc cga gaa gcg tta aga cat atg tat gct aca act cca caa cgt       764
Pro Ala Arg Glu Ala Leu Arg His Met Tyr Ala Thr Thr Pro Gln Arg
    165                 170                 175 tta tat ggc tac gat gaa cta ctt act gaa cta ctg tcc tca aac ctg       812
Leu Tyr Gly Tyr Asp Glu Leu Leu Thr Glu Leu Leu Ser Ser Asn Leu
180                 185                 190                 195 ttg gga gaa cat taatggctga tttatccaag aagctggcga aagcgcccgt           864
Leu Gly Glu His taccagcgcg ccgcaaaaga aagtggccga gacctttact accgccacgg agaagcccac    924
ccgcaccacc atttaccttc caacaagtct cgctaagcgc cttaagcatg ctgccgtcga    984
agaggagcgc agtgtctctg caatcctcgc aggactggcc gaagactggc taaacaaaga   1044
agacgactaa gtatgtttat atgtcatggc atacgacata caaacataac aacatagaaa   1104
cctaacaacg tattaactcc aagtagtcag cgctggagac catgccccat cgacacgcgg   1164
ctgcgctgct cgtggggcca gaagtggcgc aggactgatg aaagaaaccc acaagacgtt   1224
taagcgtcaa agcgtcaagc ggacacaaca tgaaaacatc aagacgttta gacccttgcg   1284
gcctttgacg ccagtcccgc cgaaacttat acattcgacg caatctatga agagatttaa   1344
ggaatgaagg agacggcttt aatgtcacca gcacggcgca gttcaagaac cactaccgga   1404
cgaaaaacaa cacgccccctc ggcggcaaca cccacaccga ccgacgagga aggcacagag   1464
cttacccggc gtacaaccat ttacctcaaa gaggaaacat ggaaatccat gaagcgcatg   1524
accgtagaaa caggagaaag cgtttctgcg tacatcgaac gactcattga taaagatgta   1584
aagcgcgtcc agaaaaagtt actccaaaac cccaaatcgc tataacacga aaacataaca   1644
acgttatagc gctttagcac taaactgtat cggggcaggt taaaaacttt tcgtgtcgca   1704
ggcacagagc aatcacactc gtgttactct ggtcgaaaac cttataaatg catgaagtcc   1764
gccaggcttg caccctgac ggacttcgct atcacccgga ggacaccgg gggaaagcac    1824 gtca atg agc tta cct tca aaa gga cga tca agc aca cct aca ggt gtg     1873
     Met Ser Leu Pro Ser Lys Gly Arg Ser Ser Thr Pro Thr Gly Val
         200                 205                 210 cgt gtt gcc caa cca ctg ccc acc cac cgc gac act ggc ggc ctg gac       1921
Arg Val Ala Gln Pro Leu Pro Thr His Arg Asp Thr Gly Gly Leu Asp
215                 220                 225                 230 gac acc ccg gca gga ttc act gat cgt gat gca ctt ata gat cat ctc       1969
Asp Thr Pro Ala Gly Phe Thr Asp Arg Asp Ala Leu Ile Asp His Leu
```

```
                       235                   240                   245
ggg cgt aaa gca atc cac gga agc aaa gac cgt gac ttc ggc aaa gct        2017
Gly Arg Lys Ala Ile His Gly Ser Lys Asp Arg Asp Phe Gly Lys Ala
            250                 255                 260 tat tac cgc cac gag gac ggt act ctt cgc ccg cgc ttg tat cgc gtg        2065
Tyr Tyr Arg His Glu Asp Gly Thr Leu Arg Pro Arg Leu Tyr Arg Val
            265                 270                 275 gat tct gag gcg ttg aca cgc tgc cag tac gtc atg ctc acc acg cag        2113
Asp Ser Glu Ala Leu Thr Arg Cys Gln Tyr Val Met Leu Thr Thr Gln
        280                 285                 290 caa tac gcc gct gta tta gtg gtc gat att gac cag ccc ggc caa tcg        2161
Gln Tyr Ala Ala Val Leu Val Val Asp Ile Asp Gln Pro Gly Gln Ser
295                 300                 305                 310 gga ggg cac cca gcg aac tta tcg cct gag gtt cgt cag aag atg gcc        2209
Gly Gly His Pro Ala Asn Leu Ser Pro Glu Val Arg Gln Lys Met Ala
            315                 320                 325 gct ctt atc gag cac aac ctt ggg ccg tcg tgg gtg ggc att aat ccc        2257
Ala Leu Ile Glu His Asn Leu Gly Pro Ser Trp Val Gly Ile Asn Pro
            330                 335                 340 caa aac ggt aaa gca cag gcg atc tgg ttg att gat ccg gtg tac gca        2305
Gln Asn Gly Lys Ala Gln Ala Ile Trp Leu Ile Asp Pro Val Tyr Ala
            345                 350                 355 gac aaa agc ggc aaa tct cgg cat atg agt ctg ctt gcc gcg acg agc        2353
Asp Lys Ser Gly Lys Ser Arg His Met Ser Leu Leu Ala Ala Thr Ser
        360                 365                 370 cgt gct ttg ggt gag ctg ttg gat cat gat ccg aat ttc tct cac cgt        2401
Arg Ala Leu Gly Glu Leu Leu Asp His Asp Pro Asn Phe Ser His Arg
375                 380                 385                 390 ttt agt cgg agc ccg ttt tat gac ggc aac gac cct acc gcc tat cgt        2449
Phe Ser Arg Ser Pro Phe Tyr Asp Gly Asn Asp Pro Thr Ala Tyr Arg
            395                 400                 405 tgg tat tgc cag cac aaa cac gtg cgc cgg tta gct gat ctt ctt aag        2497
Trp Tyr Cys Gln His Lys His Val Arg Arg Leu Ala Asp Leu Leu Lys
            410                 415                 420 gag ata cgc act atg acg ggt caa gag cag tac acc aag cct cag caa        2545
Glu Ile Arg Thr Met Thr Gly Gln Glu Gln Tyr Thr Lys Pro Gln Gln
        425                 430                 435 cag ttt tct agt ggc cgc gag ctt att aat gct gtg aaa act cgc aga        2593
Gln Phe Ser Ser Gly Arg Glu Leu Ile Asn Ala Val Lys Thr Arg Arg
    440                 445                 450 gaa gaa gcc caa gca ttt aaa gca ctt gcc cag gac gtc gag acc gaa        2641
Glu Glu Ala Gln Ala Phe Lys Ala Leu Ala Gln Asp Val Glu Thr Glu
455                 460                 465                 470 ctc agc aca gag ctt gat cag tac gac ccg gaa ctt atc gaa ggg gta        2689
Leu Ser Thr Glu Leu Asp Gln Tyr Asp Pro Glu Leu Ile Glu Gly Val
            475                 480                 485 cga gtc tta tgg att agc cag ggg cgt gct gcc cgg gat gag acg gcg        2737
Arg Val Leu Trp Ile Ser Gln Gly Arg Ala Ala Arg Asp Glu Thr Ala
            490                 495                 500 ttt cgt tac gct ttg aaa acc tgc cac cgg cta cgg gcc gca ggt gag        2785
Phe Arg Tyr Ala Leu Lys Thr Cys His Arg Leu Arg Ala Ala Gly Glu
        505                 510                 515 cgt atg act gat gcc gcg atc att gat gcc tat gag cat gcg tat aac        2833
Arg Met Thr Asp Ala Ala Ile Ile Asp Ala Tyr Glu His Ala Tyr Asn
        520                 525                 530 gtt gct cag cgc cat ggg gga gac ggc cgg gat agt gag atg ccg ccg        2881
Val Ala Gln Arg His Gly Gly Asp Gly Arg Asp Ser Glu Met Pro Pro
535                 540                 545                 550 atg cgg gat cgc cag acg atg gcg cgt cgc gtg cgc ggc tac gtg act        2929
```

-continued

| | | |
|---|---|---|
| Met Arg Asp Arg Gln Thr Met Ala Arg Arg Val Arg Gly Tyr Val Thr<br>555     560     565 | | |
| caa tct aag acc agt atg ggc gca tca gcc cct cca ggg cgt gct aca<br>Gln Ser Lys Thr Ser Met Gly Ala Ser Ala Pro Pro Gly Arg Ala Thr<br>   570     575     580 | | 2977 |
| agc act gaa cgt aaa gca tta tcc acg atg ggg cgt cga ggc ggt aaa<br>Ser Thr Glu Arg Lys Ala Leu Ser Thr Met Gly Arg Arg Gly Gly Lys<br>585     590     595 | | 3025 |
| aag gcc gca gaa cgc tgg aaa gac cgt gag agc cat tac gcg caa act<br>Lys Ala Ala Glu Arg Trp Lys Asp Arg Glu Ser His Tyr Ala Gln Thr<br>600     605     610 | | 3073 |
| gaa ttg gaa aag ctt gcc gat gcc agt aag aag cgt tca aga aaa gcc<br>Glu Leu Glu Lys Leu Ala Asp Ala Ser Lys Lys Arg Ser Arg Lys Ala<br>615     620     625     630 | | 3121 |
| aaa ggc acg cgc tta act att gcg ggc tgg gtg atg agt gtg gaa tct<br>Lys Gly Thr Arg Leu Thr Ile Ala Gly Trp Val Met Ser Val Glu Ser<br>   635     640     645 | | 3169 |
| gag aca ggt gca tgg cct act atc gct gag gcg atg gtg gag ttt tcg<br>Glu Thr Gly Ala Trp Pro Thr Ile Ala Glu Ala Met Val Glu Phe Ser<br>650     655     660 | | 3217 |
| gtc tct aga gag act gta aaa agg gcg ctt aga tct gct gga att gag<br>Val Ser Arg Glu Thr Val Lys Arg Ala Leu Arg Ser Ala Gly Ile Glu<br>665     670     675 | | 3265 |
| ctt cca cgg ggc aga cga aag acc tca aat taaatggctc acttcgtaag<br>Leu Pro Arg Gly Arg Arg Lys Thr Ser Asn<br>680     685 | | 3315 |
| caatatacgg ttccccgtgc acagcacggg ggggcttaac tcttgctctt ttaagcttta | | 3375 |
| attaaatagt tcaggttata agcaatatac ggttttcctg gtcttgtgca gggaggccac | | 3435 |
| tttacttcgg cctttgaaag tgaattgtgt ttcaaattaa aggtgcttct gaagaccttt | | 3495 |
| aatctctagg gagttttttct gtaggaggca gttgggtcta gccagggttg ataagtgatt | | 3555 |
| tcagtgagtg tccttctaga atgaaaagct tacgagtcgt ttaggcatat aacgggtgac | | 3615 |
| tagcgagttc agactttaaa agcgcaaaca aatttaatga ggtaatgcta tgagaaacgt | | 3675 |
| tcttttaact tgtccaatcc gtggcgagct tactgctact tcccttgctt ctgatgggct | | 3735 |
| tacgcctacc gaagaggcga tgaggattga tttgcttgag tttcttatag ataaacgtga | | 3795 |
| ctacccaaaa gattttattg atgttgaaac tgtggtgctg agcaatatcg gtaatgcagg | | 3855 |
| gcgcaatagt cttcgtgcgg acgtcattgt gtatgacatc ccgaagatgc aagcacgggc | | 3915 |
| catgtcacat gaagaacgac taattcatgc gacgttgatc gcagaggtga acgagaggg | | 3975 |
| gaaatacaag aaaagcgctg tttctcatca gttagttccg gcattgaagc tcgctccatc | | 4035 |
| tatgaagaca cttggaattt actgggataa cgaggaaagg ctcctctttc agaagacttt | | 4095 |
| ttcagatgaa atgctttcgg ttgaagagat caccgttgca aaactcccaa agtggggttt | | 4155 |
| ttccctcaca ggaaaccccc tcacttacaa tcaactttcc tctccgaaag atttgttcaa | | 4215 |
| aactctaagt ggtgtcgctg acattatgcg gagtggtgga gtcgaagata acaactgcg | | 4275 |
| ctatatcgaa acagtcaagt tgcttcttgc taggtataca gatgaacgca gtgcttctga | | 4335 |
| tccacaagat aaaaacggcg gagttcttgt gatgcagatt ttgtctgacg gtgaccctaa | | 4395 |
| ctttcgaaac cgaatggatg atctctataa gcgttcagcc gcgcgttaca gcaaagcgaa | | 4455 |
| gactctattc gcgaataaga cgtcacagct tgatgatgcc acgctccgtc aattagtggt | | 4515 |
| aaagattcaa ggttttcggt taac | | 4539 |

<210> SEQ ID NO 2

```
<211> LENGTH: 199
<212> TYPE: PRT
<213> ORGANISM: Corynebacterium glutamicum

<400> SEQUENCE: 2

Met Ser Ile Leu Thr Ile Ala His Thr Lys Gly Gly Val Gly Lys Thr
  1               5                  10                  15

Thr Ser Ala Val Leu Leu Cys Ala Ala Ala His Ala Arg Gly Leu Ala
             20                  25                  30

Val Thr Leu Ile Asp Ser Asp Ala Gln Gly Thr Ala Thr Ala Trp Ala
         35                  40                  45

His Ala Ala Glu Glu Ala Gly Asp Thr Phe Pro Trp Pro Ile Ile Thr
     50                  55                  60

Ala Ala Thr Pro Ala His Leu Ala Arg Thr Leu Asp Gly His Asn Gly
 65                  70                  75                  80

Leu Val Ile Val Asp Thr Pro Gly Gly Tyr Glu Val Ile Glu Thr
                 85                  90                  95

Ala Ile Glu Ala Gly Asp Leu Ile Leu Ile Pro Thr Ser Ala Ser Pro
                100                 105                 110

Leu Asp Ile Asn Arg Val Trp Pro Thr Val Glu Ala Thr Ser His Lys
            115                 120                 125

Pro Ala Val Cys Leu Ser Gln Ile Asp Ser Arg Thr Thr Leu Pro
        130                 135                 140

Lys Ile Ala Arg Thr Ala Leu Glu Asn Glu Gly Val Val Ala Glu
145                 150                 155                 160

Thr Glu Ile Pro Ala Arg Glu Ala Leu Arg His Met Tyr Ala Thr Thr
                165                 170                 175

Pro Gln Arg Leu Tyr Gly Tyr Asp Glu Leu Leu Thr Glu Leu Leu Ser
            180                 185                 190

Ser Asn Leu Leu Gly Glu His
        195

<210> SEQ ID NO 3
<211> LENGTH: 489
<212> TYPE: PRT
<213> ORGANISM: Corynebacterium glutamicum

<400> SEQUENCE: 3

Met Ser Leu Pro Ser Lys Gly Arg Ser Ser Thr Pro Thr Gly Val Arg
  1               5                  10                  15

Val Ala Gln Pro Leu Pro Thr His Arg Asp Thr Gly Gly Leu Asp Asp
             20                  25                  30

Thr Pro Ala Gly Phe Thr Asp Arg Asp Ala Leu Ile Asp His Leu Gly
         35                  40                  45

Arg Lys Ala Ile His Gly Ser Lys Asp Arg Asp Phe Gly Lys Ala Tyr
     50                  55                  60

Tyr Arg His Glu Asp Gly Thr Leu Arg Pro Arg Leu Tyr Arg Val Asp
 65                  70                  75                  80

Ser Glu Ala Leu Thr Arg Cys Gln Tyr Val Met Leu Thr Thr Gln Gln
                 85                  90                  95

Tyr Ala Ala Val Leu Val Asp Ile Asp Gln Pro Gly Gln Ser Gly
                100                 105                 110

Gly His Pro Ala Asn Leu Ser Pro Glu Val Arg Gln Lys Met Ala Ala
            115                 120                 125

Leu Ile Glu His Asn Leu Gly Pro Ser Trp Val Gly Ile Asn Pro Gln
        130                 135                 140
```

```
Asn Gly Lys Ala Gln Ala Ile Trp Leu Ile Asp Pro Val Tyr Ala Asp
145                 150                 155                 160

Lys Ser Gly Lys Ser Arg His Met Ser Leu Leu Ala Ala Thr Ser Arg
            165                 170                 175

Ala Leu Gly Glu Leu Leu Asp His Asp Pro Asn Phe Ser His Arg Phe
        180                 185                 190

Ser Arg Ser Pro Phe Tyr Asp Gly Asn Asp Pro Thr Ala Tyr Arg Trp
    195                 200                 205

Tyr Cys Gln His Lys His Val Arg Arg Leu Ala Asp Leu Leu Lys Glu
210                 215                 220

Ile Arg Thr Met Thr Gly Gln Glu Gln Tyr Thr Lys Pro Gln Gln Gln
225                 230                 235                 240

Phe Ser Ser Gly Arg Glu Leu Ile Asn Ala Val Lys Thr Arg Arg Glu
            245                 250                 255

Glu Ala Gln Ala Phe Lys Ala Leu Ala Gln Asp Val Glu Thr Glu Leu
        260                 265                 270

Ser Thr Glu Leu Asp Gln Tyr Asp Pro Glu Leu Ile Glu Gly Val Arg
    275                 280                 285

Val Leu Trp Ile Ser Gln Gly Arg Ala Ala Arg Asp Glu Thr Ala Phe
290                 295                 300

Arg Tyr Ala Leu Lys Thr Cys His Arg Leu Arg Ala Ala Gly Glu Arg
305                 310                 315                 320

Met Thr Asp Ala Ala Ile Ile Asp Ala Tyr Glu His Ala Tyr Asn Val
            325                 330                 335

Ala Gln Arg His Gly Gly Asp Gly Arg Asp Ser Glu Met Pro Pro Met
        340                 345                 350

Arg Asp Arg Gln Thr Met Ala Arg Val Arg Gly Tyr Val Thr Gln
    355                 360                 365

Ser Lys Thr Ser Met Gly Ala Ser Ala Pro Pro Gly Arg Ala Thr Ser
    370                 375                 380

Thr Glu Arg Lys Ala Leu Ser Thr Met Gly Arg Arg Gly Gly Lys Lys
385                 390                 395                 400

Ala Ala Glu Arg Trp Lys Asp Arg Glu Ser His Tyr Ala Gln Thr Glu
            405                 410                 415

Leu Glu Lys Leu Ala Asp Ala Ser Lys Lys Arg Ser Arg Lys Ala Lys
        420                 425                 430

Gly Thr Arg Leu Thr Ile Ala Gly Trp Val Met Ser Val Glu Ser Glu
    435                 440                 445

Thr Gly Ala Trp Pro Thr Ile Ala Glu Ala Met Val Glu Phe Ser Val
450                 455                 460

Ser Arg Glu Thr Val Lys Arg Ala Leu Arg Ser Ala Gly Ile Glu Leu
465                 470                 475                 480

Pro Arg Gly Arg Arg Lys Thr Ser Asn
            485
```

<210> SEQ ID NO 4
<211> LENGTH: 1856
<212> TYPE: DNA
<213> ORGANISM: Corynebacterium glutamicum
<220> FEATURE:
<221> NAME/KEY: CDS
<222> LOCATION: (338)..(1291)
<223> OTHER INFORMATION: repA

<400> SEQUENCE: 4

```
gcatgccaat aaaagtcaac cgccgtggc cacccaaaac cagagtgtaa ataaacattg      60
agatagcttg atacctagac atctttccgc ctgatacca gacattaaga cgtctagatt    120
gcttgctatc tacaacccct cacccaggga ctaaattaat attccaacaa agaaggactc    180
ccatgttttc gtattctaaa tatcgaatac ctgatcggcg tttcgggcag ctatgtcaca    240
tgtgactgct acgatcaggg gaaaattaaa agacctggca ctgccgcaaa cagtccaggt    300 cagtgacccca cactatttct aagagacatg aggattt atg gat gat cat act ctg    355
                                           Met Asp Asp His Thr Leu
                                             1               5 cca cag cca gat tcg ggc aac tca gat cca att agc gat ttg gaa gcg     403
Pro Gln Pro Asp Ser Gly Asn Ser Asp Pro Ile Ser Asp Leu Glu Ala
         10                  15                  20 cgc ctc gca gag atc gag gct ggc ctc ggc gat ccg ctc agt ttc acg     451
Arg Leu Ala Glu Ile Glu Ala Gly Leu Gly Asp Pro Leu Ser Phe Thr
             25                  30                  35 tca aaa acc ctg atc cag gca act ttt cca cac agt gca aaa gcc gga     499
Ser Lys Thr Leu Ile Gln Ala Thr Phe Pro His Ser Ala Lys Ala Gly
     40                  45                  50 aaa gaa ctt gtc ctg gtt aac ggc cat acg aca gtc acg atg tac agc     547
Lys Glu Leu Val Leu Val Asn Gly His Thr Thr Val Thr Met Tyr Ser
 55                  60                  65                  70 cgc cac ggc ctg cca tat ggc tca tgg cca cgg ctc att atg tgc tgg     595
Arg His Gly Leu Pro Tyr Gly Ser Trp Pro Arg Leu Ile Met Cys Trp
                 75                  80                  85 cta aca agg gaa gcc ctt cgc cgc caa aat ctc cca att gat gag gct     643
Leu Thr Arg Glu Ala Leu Arg Arg Gln Asn Leu Pro Ile Asp Glu Ala
             90                  95                 100 cgt gaa atc ccg ctt aat tca agc ttg agt ggt ttt atg cgg gaa gtt     691
Arg Glu Ile Pro Leu Asn Ser Ser Leu Ser Gly Phe Met Arg Glu Val
         105                 110                 115 ggc atc gga cgt gca acc gga ggg gag cgt ggc acg atc acc gcg ctg     739
Gly Ile Gly Arg Ala Thr Gly Gly Glu Arg Gly Thr Ile Thr Ala Leu
     120                 125                 130 aaa aag cag atg cgg tct ctt ttc tcc act tca atc ggc att gac atc     787
Lys Lys Gln Met Arg Ser Leu Phe Ser Thr Ser Ile Gly Ile Asp Ile
135                 140                 145                 150 aaa gga gat gac gac ctt aag ctc ctg gat ctt gat gaa tca gtt atc     835
Lys Gly Asp Asp Asp Leu Lys Leu Leu Asp Leu Asp Glu Ser Val Ile
                 155                 160                 165 gct gag cgg acg gag atg tgg tgg acg ccg cga ccc cac gat gac atc     883
Ala Glu Arg Thr Glu Met Trp Trp Thr Pro Arg Pro His Asp Asp Ile
             170                 175                 180 gat ttt gag gga tat att cga ctc tcc gct act ttc tac tca gat ctc     931
Asp Phe Glu Gly Tyr Ile Arg Leu Ser Ala Thr Phe Tyr Ser Asp Leu
         185                 190                 195 atc aaa tca gcc gtc ccc ctc gac acc cga atc ctc cgc agt cta aag     979
Ile Lys Ser Ala Val Pro Leu Asp Thr Arg Ile Leu Arg Ser Leu Lys
     200                 205                 210 aaa tct ccg atg gcc atc gat gtc tac tct tgg ctc acc tac aga gtt    1027
Lys Ser Pro Met Ala Ile Asp Val Tyr Ser Trp Leu Thr Tyr Arg Val
215                 220                 225                 230 tca tac ttg cgc tac ccc aca gta att aag tgg gat cag atc caa gga    1075
Ser Tyr Leu Arg Tyr Pro Thr Val Ile Lys Trp Asp Gln Ile Gln Gly
                 235                 240                 245 cag cta ggc gct ggc tac cct gac act tct caa gga atg cga aac ttc    1123
Gln Leu Gly Ala Gly Tyr Pro Asp Thr Ser Gln Gly Met Arg Asn Phe
             250                 255                 260 agg aag aaa ttt ttg atc gcc ctc aac aaa gtc att gac gta tgg ccc    1171
Arg Lys Lys Phe Leu Ile Ala Leu Asn Lys Val Ile Asp Val Trp Pro
```

-continued

```
Arg Lys Lys Phe Leu Ile Ala Leu Asn Lys Val Ile Asp Val Trp Pro
            265                 270                 275 acc gac tcg atc agc atc gta aaa aac gga att cta ctg acc cct ggt      1219
Thr Asp Ser Ile Ser Ile Val Lys Asn Gly Ile Leu Leu Thr Pro Gly
        280                 285                 290 tca cca agc gtt ccc cgc aga gca cag gat gag ttc caa aaa cgc ttt      1267
Ser Pro Ser Val Pro Arg Arg Ala Gln Asp Glu Phe Gln Lys Arg Phe
295                 300                 305                 310 tcg att ggt gat gat cca ctt ttt taaatcgata agtccccgca cttaggagtg     1321
Ser Ile Gly Asp Asp Pro Leu Phe
                315 cggggatttt tcatgcccaa atacgtgcgc agtaacggta ccgcccgtgc gcagtaacgg    1381 taccgcccgt gcgcagtaac ggtaccgccc gtgcgcagta acggtaccgc ccgtgcgcag    1441 taacggtacc ggaacctatt atatattagc aggtcaaagt atgtttccaa ggtctcccct    1501 ataggtcctt tagggcctat acaaccttta caactaccta tatgcaaaga aacttcaatt    1561 catgttcggg tagcagaaaa ttgtccgaaa ctagcgttac acgaaatgca aatacgtatc    1621 taagtatata actgaaatat aaaaacggca gaccgtaatt attaattaga aaacccgccc    1681 tggaattatc caaagcggga ataaaagggt taagggaaac tagcgagcat tttctgattt    1741 ctcggcatta ggaccgaccc acttccctct acgaccaaac tgttttgtgt cagagggttg    1801 tgcacactca gtgtcatgac cttatgcaca ctcaatctca tgaccttgtg catgc         1856
```

<210> SEQ ID NO 5
<211> LENGTH: 318
<212> TYPE: PRT
<213> ORGANISM: Corynebacterium glutamicum

<400> SEQUENCE: 5

```
Met Asp Asp His Thr Leu Pro Gln Pro Asp Ser Gly Asn Ser Asp Pro
 1               5                  10                  15

Ile Ser Asp Leu Glu Ala Arg Leu Ala Glu Ile Glu Ala Gly Leu Gly
            20                  25                  30

Asp Pro Leu Ser Phe Thr Ser Lys Thr Leu Ile Gln Ala Thr Phe Pro
        35                  40                  45

His Ser Ala Lys Ala Gly Lys Glu Leu Val Leu Val Asn Gly His Thr
    50                  55                  60

Thr Val Thr Met Tyr Ser Arg His Gly Leu Pro Tyr Gly Ser Trp Pro
65                  70                  75                  80

Arg Leu Ile Met Cys Trp Leu Thr Arg Glu Ala Leu Arg Arg Gln Asn
                85                  90                  95

Leu Pro Ile Asp Glu Ala Arg Glu Ile Pro Leu Asn Ser Ser Leu Ser
            100                 105                 110

Gly Phe Met Arg Glu Val Gly Ile Gly Arg Ala Thr Gly Gly Glu Arg
        115                 120                 125

Gly Thr Ile Thr Ala Leu Lys Lys Gln Met Arg Ser Leu Phe Ser Thr
    130                 135                 140

Ser Ile Gly Ile Asp Ile Lys Gly Asp Asp Leu Lys Leu Leu Asp
145                 150                 155                 160

Leu Asp Glu Ser Val Ile Ala Glu Arg Thr Glu Met Trp Trp Thr Pro
                165                 170                 175

Arg Pro His Asp Asp Ile Asp Phe Glu Gly Tyr Ile Arg Leu Ser Ala
            180                 185                 190

Thr Phe Tyr Ser Asp Leu Ile Lys Ser Ala Val Pro Leu Asp Thr Arg
        195                 200                 205
```

```
Ile Leu Arg Ser Leu Lys Lys Ser Pro Met Ala Ile Asp Val Tyr Ser
        210                 215                 220

Trp Leu Thr Tyr Arg Val Ser Tyr Leu Arg Tyr Pro Thr Val Ile Lys
225                 230                 235                 240

Trp Asp Gln Ile Gln Gly Gln Leu Gly Ala Gly Tyr Pro Asp Thr Ser
                245                 250                 255

Gln Gly Met Arg Asn Phe Arg Lys Lys Phe Leu Ile Ala Leu Asn Lys
            260                 265                 270

Val Ile Asp Val Trp Pro Thr Asp Ser Ile Ser Ile Val Lys Asn Gly
        275                 280                 285

Ile Leu Leu Thr Pro Gly Ser Pro Ser Val Pro Arg Arg Ala Gln Asp
    290                 295                 300

Glu Phe Gln Lys Arg Phe Ser Ile Gly Asp Asp Pro Leu Phe
305                 310                 315

<210> SEQ ID NO 6
<211> LENGTH: 7316
<212> TYPE: DNA
<213> ORGANISM: Corynebacterium glutamicum
<220> FEATURE:
<221> NAME/KEY: gene
<222> LOCATION: Complement((1447)..(2013))
<223> OTHER INFORMATION: tetR
<221> NAME/KEY: CDS
<222> LOCATION: (2124)..(3272)
<223> OTHER INFORMATION: tetA
<221> NAME/KEY: CDS
<222> LOCATION: (5882)..(6718)
<223> OTHER INFORMATION: aadA

<400> SEQUENCE: 6
aagcttgagc atgcttggcg gagattggac ggacggaacg atgacggatt tcaagtggcg     60
ccatttccag ggtgatgtga tcctgtgggc ggtgcgctgg tattgtcgct atccgatcag    120
ctatcgcgac cttgaggaaa tgctggcgga acgcggcatt tcggtcgacc atacgacgat    180
ctatcgctgg gtccagtgct acgccccgga gatgggagaag cggctgcgct ggttctggcg    240
gcgtggcttt gatccgagct ggcgcctgga tgaaacctac gtcaaggtgc ggggcaagtg    300
gacctacctg taccgggcag tcgacaagcg gggcgacacg atcgatttct acctgtcgcc    360
gacccgcagc gccaaggcag cgaagcggtt cctgggcaag gccctgcgag gcctgaagca    420
ctgggaaaag cctgccacgc tcaataccga caaagcgccg agctatggtg cagcgatcac    480
cgaattgaag cgcgaaggaa agctggaccg ggagacggcc caccggcagg tgaagtatct    540
caataacgtg atcgaggccg atcacggaaa gctcaagata ctgatcaagc cggtgcgcgg    600
tttcaaatcg atccccacgg cctatgccac gatcaaggga ttcgaagtca tgcgagccct    660
gcgcaaagga caggctcgcc cctggtgcct gcagcccggc atcaggggcg aggtgcgcct    720
tgtggagaga gctttttggca ttgggccctc ggcgctgacg gaggccatgg gcatgctcaa    780
ccaccatttc gcagcagccc cctgatcggc gcagagcgac agcctacctc tgactgccgc    840
caatctttgc aacagagcct tgcgtcaat gcagggagat agcgaagagc gcgcttcaac    900
ggagatgctc gaatgggtcc acgacggatt ggagtccgtg gtcgcggcag acgtagatga    960
ttcgcacgcc gtaccgtcg cgccgctcg gctcggggtc gcattctgcg cggcagacgt   1020
tacagagccg gtgctcgttg ctcccccaga ccgtgacctc gatatcgtcg gggatctcca   1080
ttccgtcgaa ctccatatgc ggaggttagc tgtcgcggat tgagtcgtgt caagatgcgg   1140
caccgatgct aaaccgccgt tacctatggt catcgcgccg gtcgcgcact cgacgcttag   1200
```

-continued

```
ttcttgaggt actcgaggac ggcgatgacg cgcttgttcc ctgtgcgctc gttaaggtcg    1260
agcatggtga agatgctgct gatgtgccgt tccgcgatcg cgacgcgaca tgcacacggt    1320
ccctgatttg ctcgtttgtg agccccgtag ccatgagcga atcgtcagta tcgcggagga    1380
ggtgctgcgg gagcgggaaa ggattgacct tactgacgca gagacccaaa gtgcgagcat    1440
ccctcatcgc tttgatgcca gcccttcaac cattgcaact aacccgaact cgaaatctag    1500
gtcttgatcg acaggctcac atccgttgtc gagcgctgtt tgttcttcta gtacgaaacc    1560
gaccgtatag cggctgatag ccatgagagc tcggaccgca gagccctcag cgaatccttc    1620
ggacacgaga aactcgatct gactttcggg ggcatccgag cccgctggca tctggtcact    1680
cttttgacgg tgaaactctg cgtgcagccg tgctccatcc cggactgcca gaagcgctgt    1740
ccggaagctc cgcgcgttgc gcaggagaaa gtcgtcccag cgctcccctg actctgggag    1800
tgaggcgtgg tgttcgcgat caagcacatc agctgcgagc gatccgagca ggtgggcctt    1860
tgtccgaaag tgccagtaga gcgctggctg ctgcacccgc agatgcgcag ccagcgcccg    1920
tgtggtgaaa ccgtcgatcc ccgtgttatt gagcacatgc ctcgcaccgc gcaagactgc    1980
tgcacgatcg agtcgcgctt gtttctgagc catgcttgca ctttatcatc gataacttta    2040
tcgttgataa ggtgtcatct ctcacttccg ctcgtggctc gttggccacg gtcctcatca    2100
cggctagcct cgacgccgcc ggc atg ggc ctg gtg atg ccg att ctt ccc gca    2153
                         Met Gly Leu Val Met Pro Ile Leu Pro Ala
                          1               5                  10 ctg cta cac gag gca ggg gtc acc gct gat gcg gtt ccg ctg aac gtc    2201
Leu Leu His Glu Ala Gly Val Thr Ala Asp Ala Val Pro Leu Asn Val
             15                  20                  25 gga gtg ctg atc gcg ctc tac gcg gta atg cag ttc atc ttt gcc ccc    2249
Gly Val Leu Ile Ala Leu Tyr Ala Val Met Gln Phe Ile Phe Ala Pro
         30                  35                  40 gta ctg gga acg ctg tcg gac cga ttc ggc cgc cgc cgg gtg ctg ctt    2297
Val Leu Gly Thr Leu Ser Asp Arg Phe Gly Arg Arg Arg Val Leu Leu
     45                  50                  55 gtt tcc ctg gcc ggt gcg acc gtc gac tat ctc gtg ctc gcc acg acg    2345
Val Ser Leu Ala Gly Ala Thr Val Asp Tyr Leu Val Leu Ala Thr Thr
 60                  65                  70 tcc gct ctg tcg gtg ttc tat atc gcc cgc gca gtg gct ggg ata acc    2393
Ser Ala Leu Ser Val Phe Tyr Ile Ala Arg Ala Val Ala Gly Ile Thr
 75                  80                  85                  90 gga gcg acc aat gcg gtc acc gcc acc gtg atc gcc gac atc acg cca    2441
Gly Ala Thr Asn Ala Val Thr Ala Thr Val Ile Ala Asp Ile Thr Pro
                 95                 100                 105 ccc cac cag cgc gcc aag cgt ttc ggt tta ctc agt gcc tgc tat ggc    2489
Pro His Gln Arg Ala Lys Arg Phe Gly Leu Leu Ser Ala Cys Tyr Gly
                110                 115                 120 ggc gga atg atc gcg ggg cca gcc atg ggt gga ctg ttc ggt gcc atc    2537
Gly Gly Met Ile Ala Gly Pro Ala Met Gly Gly Leu Phe Gly Ala Ile
            125                 130                 135 tcg cca cat ctg ccg ttt ttg ctc gct gct ctt ctc tca gcg agc aat    2585
Ser Pro His Leu Pro Phe Leu Leu Ala Ala Leu Leu Ser Ala Ser Asn
        140                 145                 150 ctg gca ctc acc ttt atc ctg tta cgc gag acc cgt cct gat tcc cct    2633
Leu Ala Leu Thr Phe Ile Leu Leu Arg Glu Thr Arg Pro Asp Ser Pro
155                 160                 165                 170 gcg cgc tct gcg tcg ctc gct cag cat cgt ggt cgc ccc ggc ctc agc    2681
Ala Arg Ser Ala Ser Leu Ala Gln His Arg Gly Arg Pro Gly Leu Ser
                175                 180                 185
```

```
gcg gtg cct ggg att acc ttc cta tta atc gca ttc ggc ctt gtt caa    2729
Ala Val Pro Gly Ile Thr Phe Leu Leu Ile Ala Phe Gly Leu Val Gln
            190                 195                 200 ttc att ggg cag gct cca ggt gcg acc tgg gtg ctg ttt act gaa cac    2777
Phe Ile Gly Gln Ala Pro Gly Ala Thr Trp Val Leu Phe Thr Glu His
        205                 210                 215 cgc ctc gac tgg agt ccc gtc gaa gtt gga atc tcc ctg tcc gtt ttc    2825
Arg Leu Asp Trp Ser Pro Val Glu Val Gly Ile Ser Leu Ser Val Phe
    220                 225                 230 ggg atc gta cag gtt ctc gtg cag gcc ctc ctt act ggc cgc atc gtg    2873
Gly Ile Val Gln Val Leu Val Gln Ala Leu Leu Thr Gly Arg Ile Val
235                 240                 245                 250 gag tgg atc ggt gag gca aaa aca gtc atc atc ggg tgt att acc gac    2921
Glu Trp Ile Gly Glu Ala Lys Thr Val Ile Ile Gly Cys Ile Thr Asp
                255                 260                 265 gcc ttg ggt ctc gta ggc ctg gcg att gtc act gac gca ttt tcc atg    2969
Ala Leu Gly Leu Val Gly Leu Ala Ile Val Thr Asp Ala Phe Ser Met
            270                 275                 280 gca cct atc ttg gcg gca ctg ggg atc ggt ggc atc ggc ctc ccc gct    3017
Ala Pro Ile Leu Ala Ala Leu Gly Ile Gly Gly Ile Gly Leu Pro Ala
        285                 290                 295 ctg caa acc ctt ctc tcc cag cgc gtc gat gaa cag cac caa ggg cgc    3065
Leu Gln Thr Leu Leu Ser Gln Arg Val Asp Glu Gln His Gln Gly Arg
    300                 305                 310 ctc cag ggt gtg ctc gcc agc atc aac agc gtc aca tcg atc ttc gga    3113
Leu Gln Gly Val Leu Ala Ser Ile Asn Ser Val Thr Ser Ile Phe Gly
315                 320                 325                 330 ccg gtc gct ttc aca acg atc ttc gcg ctc act tac atc aac gcc gac    3161
Pro Val Ala Phe Thr Thr Ile Phe Ala Leu Thr Tyr Ile Asn Ala Asp
                335                 340                 345 ggc ttc ctc tgg ctc tgc gcc gca gca ctc tac gtg ccc tgc gtg att    3209
Gly Phe Leu Trp Leu Cys Ala Ala Ala Leu Tyr Val Pro Cys Val Ile
            350                 355                 360 ctc atc atg cgt ggt aca gca gcg tcc ccg aag ttc ggc tct tgg gcg    3257
Leu Ile Met Arg Gly Thr Ala Ala Ser Pro Lys Phe Gly Ser Trp Ala
        365                 370                 375 agc ggc gac tcg atg tgagttgtga gacgtgagca ggagcaacac ggcggcgaca    3312
Ser Gly Asp Ser Met
380 ctgcttcgcc atggccgact agcgagacgg cgccaccggg aaactcggca tcatctacca   3372 aggacaggtc agctgggagc ctgatagacc catcgaaatg tgcgtgccga tcgcggagaa   3432 gggccgggcg catcggatcg agccatagca ccatgagtct tcacggaagt gcgtcgacgg   3492 agacttggtt gtgaaccggg ccaagggaga gctggaggcc ctctccgagt ggcttgccga   3552 tgacatgagc tggacgctca tcgagaaatc cacacacagc ggccccagtg cagcccgaga   3612 ggtgcgcccg ccgttctccc gagcgggtgg aggtcatttc tgtcgtcacc cacggacgac   3672 gcgcttcctg cgacggctac ctcgaggctg aggaatgcg cgtccgtttc agccatgcgt    3732 tccgcttcgt cagcaccccc aagacctcga tgatcgcaga actgcgacgc tactgcatcg   3792 agacgcaggt tgactgaggc ctgtgcggac agcacgaacg acccttgagc cgtaatctg    3852 ggaaccgcag aaactacccg atcgaaacgc aactactttg ccgaccctac ggggttggct   3912 cgcggtcgtc gtccttggcc gggctctgtt gcaaaaatcg tgaagcttga gcatgcttgg   3972 cggagattgg acggacggaa cgatgacgga tttcaagtgg cgccatttcc aggtgatgt    4032 gatcctgtgg gcggtgcgct ggtattgtcg ctatccgatc agctatcgcg accttgagga   4092 aatgctggcg gaacgcggca tttcggtcga ccatacgacg atctatcgct gggtccagtg   4152
```

```
ctacgcccg gagatggaga agcggctgcg ctggttctgg cggcgtggct ttgatccgag   4212
ctggcgcctg gatgaaacct acgtcaaggt gcggggcaag tggacctacc tgtaccgggc   4272
agtcgacaag cggggcgaca cgatcgattt ctacctgtcg ccgacccgca gcgccaaggc   4332
agcgaagcgg ttcctgggca aggccctgcg aggcctgaag cactgggaaa agcctgccac   4392
gctcaatacc gacaaagcgc cgagctatgg tgcagcgatc accgaattga agcgcgaagg   4452
aaagctggac cgggagacgg cccaccggca ggtgaagtat ctcaataacg tgatcgaggc   4512
cgatcacgga aagctcaaga tactgatcaa gccggtgcgc ggtttcaaat cgatccccac   4572
ggcctatgcc acgatcaagg gattcgaagt catgcgagcc ctgcgcaaag gacaggctcg   4632
cccctggtgc ctgcagcccg gcatcagggg cgaggtgcgc cttgtggaga gcttttgg    4692 cattgggccc tcggcgctga cggaggccat gggcatgctc aaccaccatt tcgcagcagc   4752
cgcctgatcg gcgcagagcg acagcctacc tctgactgcc gccaatcttt gcaacagagc   4812
cgtcgtagag acgtcggaat ggccgagcag atcctgcacg gttcgaatgt cgtaaccgct   4872
gcggagcaag gccgtcgcga acgagtggcg gaggtgtgc ggtgtggcgg gcttcgtgat    4932
gcctgcttgt tctacggcac gtttgaaggc gcgctgaaag gtctggtcat acatgtgatg   4992
gcgacgcacg acaccgctcc gtggatcggt cgaatgcgtg tgctgcgcaa aaacccagaa   5052
ccacggccag gaatgcccgg cgcgcggata cttccgctca agggcgtcgg gaagcgcaac   5112
gccgctgcgg ccctcggcct ggtccttcag ccaccatgcc cgtgcacgcg acagctgctc   5172
gcgcaggctg ggtgccaagc tctcgggtaa catcaaggcc cgatccttgg agcccttgcc   5232
ctcccgcacg atgatcgtgc cgtgatcgaa atccagatcc ttgacccgca gttgcaaacc   5292
ctcactgatc cgcatgcccg ttccatacag aagctgggcg aacaaacgat gctcgccttc   5352
cagaaaaccg aggatgcgaa ccacttcatc cggggtcagc accaccggca agcgccgcga   5412
cggccgaggt cttccgatct cctgaagcca gggcagatcc gtgcacagca ccttgccgta   5472
gaagaacagc aaggccgcca atgcctgacg atgcgtggag accgaaacct tgcgctcgtt   5532
cgccagccag gacagaaatg cctcgacttc gctgctgccc aaggttgccg ggtgacgcac   5592
accgtggaaa cggatgaagg cacgaaccca gtggacatac gcctgttcgg ttcgtaagct   5652
ataatgcaag tagcgtatgc gctcacgcaa ctggtccaga accttgaccg aacgcagcgg   5712
tggtaacggt gcagtgctgg ttttcatggc ttgttatgac tgttttgttg tacagtctat   5772
gcctcgggca tccaagcagc aagcgcgtta cgccgtgggt cgatgtttga tgttatggag   5832
cagcaacgat gttacgcagc agggcagtcg ccctaaaaca aagttagac atg atg agc   5890
                                                     Met Met Ser
                                                             385 aac tct ata cac acc gga atc tca aga cag ctt tca cag gca cgc gat   5938
Asn Ser Ile His Thr Gly Ile Ser Arg Gln Leu Ser Gln Ala Arg Asp
        390                 395                 400 gta att aaa cgc cat ttg gca tca acg ctg aaa gcc ata cac ttg tat   5986
Val Ile Lys Arg His Leu Ala Ser Thr Leu Lys Ala Ile His Leu Tyr
            405                 410                 415 ggt tct gca att gat ggt ggc ctc aaa cca tat agc gac att gat ctg   6034
Gly Ser Ala Ile Asp Gly Gly Leu Lys Pro Tyr Ser Asp Ile Asp Leu
        420                 425                 430 ctg gtt acc gtg gat gca cgc ttg gat gaa gct acc aga cgc tcc ctg   6082
Leu Val Thr Val Asp Ala Arg Leu Asp Glu Ala Thr Arg Arg Ser Leu
435                 440                 445                 450 atg ctc gat ttc ttg aat atc tcg gca cca cca tgc gaa agc tca ata   6130
Met Leu Asp Phe Leu Asn Ile Ser Ala Pro Pro Cys Glu Ser Ser Ile
```

-continued

```
                    455                 460                 465
ctc cgg ccg cta gag gta act gtt gtt gca tgc aac gaa gta gtg cct         6178
Leu Arg Pro Leu Glu Val Thr Val Val Ala Cys Asn Glu Val Val Pro
                470                 475                 480 tgg cgt tat ccg gca cga cga gaa ctg cag ttc ggg gag tgg ctg cgg         6226
Trp Arg Tyr Pro Ala Arg Arg Glu Leu Gln Phe Gly Glu Trp Leu Arg
            485                 490                 495 gag gat att ctt gaa ggt gtc ttc gag cca gcc gcc ttg gac gcc gac         6274
Glu Asp Ile Leu Glu Gly Val Phe Glu Pro Ala Ala Leu Asp Ala Asp
        500                 505                 510 ctt gca att cta ata acg aaa gct agg caa cac agc atc gct tta gta         6322
Leu Ala Ile Leu Ile Thr Lys Ala Arg Gln His Ser Ile Ala Leu Val
    515                 520                 525                 530 ggt cca gtg gct caa aaa gtc ttc atg ccg gtg cca gag cat gac ttt         6370
Gly Pro Val Ala Gln Lys Val Phe Met Pro Val Pro Glu His Asp Phe
                535                 540                 545 ctc cag gtg ctt tcc gat acc ctt aag ctg tgg aat act cat gag gat         6418
Leu Gln Val Leu Ser Asp Thr Leu Lys Leu Trp Asn Thr His Glu Asp
            550                 555                 560 tgg gaa aat gag gag cgg aac atc gta ctc acg tta gct cgg atc tgg         6466
Trp Glu Asn Glu Glu Arg Asn Ile Val Leu Thr Leu Ala Arg Ile Trp
        565                 570                 575 tat agc act gaa act gga gga atc gtc ccc aag gat gtg gcc gcc gaa         6514
Tyr Ser Thr Glu Thr Gly Gly Ile Val Pro Lys Asp Val Ala Ala Glu
    580                 585                 590 tgg gtt tta gag cgc ttg cca gct gag cat aag cca ata ctg gtt gag         6562
Trp Val Leu Glu Arg Leu Pro Ala Glu His Lys Pro Ile Leu Val Glu
595                 600                 605                 610 gcg cgg caa gcc tat ctt ggg ctt tgc aag gat agt ctt gct ttg cgt         6610
Ala Arg Gln Ala Tyr Leu Gly Leu Cys Lys Asp Ser Leu Ala Leu Arg
                615                 620                 625 gca gat gag act tcg gcg ttc att ggc tat gca aag tct gcg gtc gct         6658
Ala Asp Glu Thr Ser Ala Phe Ile Gly Tyr Ala Lys Ser Ala Val Ala
            630                 635                 640 gat ttg ctc gaa aag cga aaa tct caa act tcg cat att tgc gat ggc         6706
Asp Leu Leu Glu Lys Arg Lys Ser Gln Thr Ser His Ile Cys Asp Gly
        645                 650                 655 gcc aag aac gtc taacgtctaa ctattcattt aagccgaagc cgcttcgcgg             6758
Ala Lys Asn Val
    660 ctcggcttaa ttcaggcgtt agatgcacta agcacataat tgctcacagc caaactatca      6818 ggtcaagtct gcttttatta tttttaagcg tgcataataa gccctacaca aattgggaga      6878 tatatcatga aaggctggct ttttcttgtt atcgcaatag ttggcgaagt aatcgcaaca      6938 tccgcattaa aatctagcga gggctttact aagcttgccc cttccgccgt tgtcataatc      6998 ggttatggca tcgcatttta ttttctttct ctggttctga aatccatccc tgtcggtgtt      7058 gcttatgcag tctggtcggg actcggcgtc gtcataatta cagccattgc ctggttgctt      7118 catgggcaaa agcttgatgc gtggggcttt gtaggtatgg ggctcataat tgctgccttt      7178 ttgctcgccc gatccccatc gtggaagtcg ctgcggaggc cgacgccatg gtgacggtgt      7238 tcggcattct gaatctcacc gaggactcct tcttcgatga gagccggcgg ctagaccccg      7298 ccggcgctgt caccgcgg                                                     7316
```

<210> SEQ ID NO 7
<211> LENGTH: 383
<212> TYPE: PRT
<213> ORGANISM: Corynebacterium glutamicum

```
<400> SEQUENCE: 7

Met Gly Leu Val Met Pro Ile Leu Pro Ala Leu Leu His Glu Ala Gly
 1               5                  10                  15

Val Thr Ala Asp Ala Val Pro Leu Asn Val Gly Val Leu Ile Ala Leu
             20                  25                  30

Tyr Ala Val Met Gln Phe Ile Phe Ala Pro Val Leu Gly Thr Leu Ser
             35                  40                  45

Asp Arg Phe Gly Arg Arg Val Leu Leu Val Ser Leu Ala Gly Ala
 50                  55                  60

Thr Val Asp Tyr Leu Val Leu Ala Thr Thr Ser Ala Leu Ser Val Phe
 65                  70                  75                  80

Tyr Ile Ala Arg Ala Val Ala Gly Ile Thr Gly Ala Thr Asn Ala Val
             85                  90                  95

Thr Ala Thr Val Ile Ala Asp Ile Thr Pro Pro His Gln Arg Ala Lys
            100                 105                 110

Arg Phe Gly Leu Leu Ser Ala Cys Tyr Gly Gly Met Ile Ala Gly
            115                 120                 125

Pro Ala Met Gly Gly Leu Phe Gly Ala Ile Ser Pro His Leu Pro Phe
    130                 135                 140

Leu Leu Ala Ala Leu Leu Ser Ala Ser Asn Leu Ala Leu Thr Phe Ile
145                 150                 155                 160

Leu Leu Arg Glu Thr Arg Pro Asp Ser Pro Ala Arg Ser Ala Ser Leu
                165                 170                 175

Ala Gln His Arg Gly Arg Pro Gly Leu Ser Ala Val Pro Gly Ile Thr
            180                 185                 190

Phe Leu Leu Ile Ala Phe Gly Leu Val Gln Phe Ile Gly Gln Ala Pro
            195                 200                 205

Gly Ala Thr Trp Val Leu Phe Thr Glu His Arg Leu Asp Trp Ser Pro
    210                 215                 220

Val Glu Val Gly Ile Ser Leu Ser Val Phe Gly Ile Val Gln Val Leu
225                 230                 235                 240

Val Gln Ala Leu Leu Thr Gly Arg Ile Val Glu Trp Ile Gly Glu Ala
                245                 250                 255

Lys Thr Val Ile Ile Gly Cys Ile Thr Asp Ala Leu Gly Leu Val Gly
                260                 265                 270

Leu Ala Ile Val Thr Asp Ala Phe Ser Met Ala Pro Ile Leu Ala Ala
    275                 280                 285

Leu Gly Ile Gly Gly Ile Gly Leu Pro Ala Leu Gln Thr Leu Leu Ser
    290                 295                 300

Gln Arg Val Asp Glu Gln His Gln Gly Arg Leu Gln Gly Val Leu Ala
305                 310                 315                 320

Ser Ile Asn Ser Val Thr Ser Ile Phe Gly Pro Val Ala Phe Thr Thr
                325                 330                 335

Ile Phe Ala Leu Thr Tyr Ile Asn Ala Asp Gly Phe Leu Trp Leu Cys
            340                 345                 350

Ala Ala Ala Leu Tyr Val Pro Cys Val Ile Leu Ile Met Arg Gly Thr
            355                 360                 365

Ala Ala Ser Pro Lys Phe Gly Ser Trp Ala Ser Gly Asp Ser Met
    370                 375                 380

<210> SEQ ID NO 8
<211> LENGTH: 279
<212> TYPE: PRT
```

<213> ORGANISM: Corynebacterium glutamicum

<400> SEQUENCE: 8

```
Met Met Ser Asn Ser Ile His Thr Gly Ile Ser Arg Gln Leu Ser Gln
  1               5                  10                  15

Ala Arg Asp Val Ile Lys Arg His Leu Ala Ser Thr Leu Lys Ala Ile
                 20                  25                  30

His Leu Tyr Gly Ser Ala Ile Asp Gly Gly Leu Lys Pro Tyr Ser Asp
             35                  40                  45

Ile Asp Leu Leu Val Thr Val Asp Ala Arg Leu Asp Glu Ala Thr Arg
 50                  55                  60

Arg Ser Leu Met Leu Asp Phe Leu Asn Ile Ser Ala Pro Pro Cys Glu
 65                  70                  75                  80

Ser Ser Ile Leu Arg Pro Leu Glu Val Thr Val Ala Cys Asn Glu
                 85                  90                  95

Val Val Pro Trp Arg Tyr Pro Ala Arg Arg Glu Leu Gln Phe Gly Glu
                100                 105                 110

Trp Leu Arg Glu Asp Ile Leu Glu Gly Val Phe Glu Pro Ala Ala Leu
            115                 120                 125

Asp Ala Asp Leu Ala Ile Leu Ile Thr Lys Ala Arg Gln His Ser Ile
130                 135                 140

Ala Leu Val Gly Pro Val Ala Gln Lys Val Phe Met Pro Val Pro Glu
145                 150                 155                 160

His Asp Phe Leu Gln Val Leu Ser Asp Thr Leu Lys Leu Trp Asn Thr
                165                 170                 175

His Glu Asp Trp Glu Asn Glu Glu Arg Asn Ile Val Leu Thr Leu Ala
            180                 185                 190

Arg Ile Trp Tyr Ser Thr Glu Thr Gly Ile Val Pro Lys Asp Val
        195                 200                 205

Ala Ala Glu Trp Val Leu Glu Arg Leu Pro Ala Glu His Lys Pro Ile
210                 215                 220

Leu Val Glu Ala Arg Gln Ala Tyr Leu Gly Leu Cys Lys Asp Ser Leu
225                 230                 235                 240

Ala Leu Arg Ala Asp Glu Thr Ser Ala Phe Ile Gly Tyr Ala Lys Ser
                245                 250                 255

Ala Val Ala Asp Leu Leu Glu Lys Arg Lys Ser Gln Thr Ser His Ile
            260                 265                 270

Cys Asp Gly Ala Lys Asn Val
        275
```

<210> SEQ ID NO 9
<211> LENGTH: 570
<212> TYPE: DNA
<213> ORGANISM: Corynebacterium glutamicum
<220> FEATURE:
<221> NAME/KEY: CDS
<222> LOCATION: (1)..(567)
<223> OTHER INFORMATION: tetR

<400> SEQUENCE: 9

```
atg gct cag aaa caa gcg cga ctc gat cgt gca gca gtc ttg cgc ggt    48
Met Ala Gln Lys Gln Ala Arg Leu Asp Arg Ala Ala Val Leu Arg Gly
  1               5                  10                  15 gcg agg cat gtg ctc aat aac acg ggg atc gac ggt ttc acc aca cgg    96
Ala Arg His Val Leu Asn Asn Thr Gly Ile Asp Gly Phe Thr Thr Arg
                 20                  25                  30 gcg ctg gct gcg cat ctg cgg gtg cag cag cca gcg ctc tac tgg cac   144
Ala Leu Ala Ala His Leu Arg Val Gln Gln Pro Ala Leu Tyr Trp His
```

```
Ala Leu Ala Ala His Leu Arg Val Gln Gln Pro Ala Leu Tyr Trp His
            35                  40                  45 ttt cgg aca aag gcc cac ctg ctc gga tcg ctc gca gct gat gtg ctt      192
Phe Arg Thr Lys Ala His Leu Leu Gly Ser Leu Ala Ala Asp Val Leu
 50                  55                  60 gat cgc gaa cac cac gcc tca ctc cca gag tca ggg gag cgc tgg gac      240
Asp Arg Glu His His Ala Ser Leu Pro Glu Ser Gly Glu Arg Trp Asp
 65                  70                  75                  80 gac ttt ctc ctg cgc aac gcg cgg agc ttc cgg aca gcg ctt ctg gca      288
Asp Phe Leu Leu Arg Asn Ala Arg Ser Phe Arg Thr Ala Leu Leu Ala
                 85                  90                  95 gtc cgg gat gga gca cgg ctg cac gca gag ttt cac cgt caa aag agt      336
Val Arg Asp Gly Ala Arg Leu His Ala Glu Phe His Arg Gln Lys Ser
            100                 105                 110 gac cag atg cca gcg ggc tcg gat gcc ccc gaa agt cag atc gag ttt      384
Asp Gln Met Pro Ala Gly Ser Asp Ala Pro Glu Ser Gln Ile Glu Phe
        115                 120                 125 ctc gtg tcc gaa gga ttc gct gag ggc tct gcg gtc cga gct ctc atg      432
Leu Val Ser Glu Gly Phe Ala Glu Gly Ser Ala Val Arg Ala Leu Met
    130                 135                 140 gct atc agc cgc tat acg gtc ggt ttc gta cta gaa gaa caa aca gcg      480
Ala Ile Ser Arg Tyr Thr Val Gly Phe Val Leu Glu Glu Gln Thr Ala
145                 150                 155                 160 ctc gac aac gga tgt gag cct gtc gat caa gac cta gat ttc gag ttc      528
Leu Asp Asn Gly Cys Glu Pro Val Asp Gln Asp Leu Asp Phe Glu Phe
                165                 170                 175 ggg tta gtt gca atg gtt gaa ggg ctg gca tca aag cga tga              570
Gly Leu Val Ala Met Val Glu Gly Leu Ala Ser Lys Arg
            180                 185

<210> SEQ ID NO 10
<211> LENGTH: 189
<212> TYPE: PRT
<213> ORGANISM: Corynebacterium glutamicum

<400> SEQUENCE: 10

Met Ala Gln Lys Gln Ala Arg Leu Asp Arg Ala Ala Val Leu Arg Gly
 1               5                  10                  15

Ala Arg His Val Leu Asn Asn Thr Gly Ile Asp Gly Phe Thr Thr Arg
            20                  25                  30

Ala Leu Ala Ala His Leu Arg Val Gln Gln Pro Ala Leu Tyr Trp His
            35                  40                  45

Phe Arg Thr Lys Ala His Leu Leu Gly Ser Leu Ala Ala Asp Val Leu
 50                  55                  60

Asp Arg Glu His His Ala Ser Leu Pro Glu Ser Gly Glu Arg Trp Asp
 65                  70                  75                  80

Asp Phe Leu Leu Arg Asn Ala Arg Ser Phe Arg Thr Ala Leu Leu Ala
                 85                  90                  95

Val Arg Asp Gly Ala Arg Leu His Ala Glu Phe His Arg Gln Lys Ser
            100                 105                 110

Asp Gln Met Pro Ala Gly Ser Asp Ala Pro Glu Ser Gln Ile Glu Phe
        115                 120                 125

Leu Val Ser Glu Gly Phe Ala Glu Gly Ser Ala Val Arg Ala Leu Met
    130                 135                 140

Ala Ile Ser Arg Tyr Thr Val Gly Phe Val Leu Glu Glu Gln Thr Ala
145                 150                 155                 160
```

```
Leu Asp Asn Gly Cys Glu Pro Val Asp Gln Asp Leu Asp Phe Glu Phe
            165                 170                 175

Gly Leu Val Ala Met Val Glu Gly Leu Ala Ser Lys Arg
            180                 185
```

PLASMIDS FROM *CORYNEBACTERIUM GLUTAMICUM* AND USE THEREOF

This application claims priority from German Application No. DE 199 53 206.0, filed on Nov. 5, 1999, the subject matter of which is hereby incorporated herein by reference.

BACKGROUND OF THE INVENTION

1. Field of the Invention

The present invention provides the novel plasmids pTET3 and pCRY4 and the use thereof for the production of vector plasmids.

2. Background Information

Naturally occurring plasmids and plasmid vectors produced therefrom are vital to the improvement of the production characteristics of coryneform bacteria. Constructing plasmid vectors for this group of industrially significant bacteria is substantially based on cryptic plasmids, which are provided with suitable selection markers capable of functioning in Corynebacteria or Brevibacteria (U.S. Pat. No. 5,158,891 and U.S. Pat. No. 4,500,640). These plasmid vectors may be used for cloning and amplifying genes which are involved in the production of L-amino acids, vitamins or nucleotides. Expression of these particular genes may have a positive influence on the production of the desired substances. Thus, for example, cloning a DNA fragment which encodes a protein for a lysine exporter resulted in an improvement in the fermentative production of L-lysine with *Corynebacterium glutamicum* strain MH20-22B (DE-A 19548222).

In contrast with the known and equally industrially significant bacterium *Escherichia coli*, only a limited number of natural plasmids and suitable selection markers are available for developing cloning and expression vectors for Corynebacteria and Brevibacteria. Many plasmids known by different names prove to be identical on more detailed analysis of their genetic organisation. These plasmid isolates have thus been classed in two groups (Sonnen et al., Gene 107, 69–74 (1991)).

The pBL1 group includes the plasmids pAM286 from *Corynebacterium glutamicum* AJ11560 (EP-A 0093611), pAM330 from *Brevibacterium lactofermentum* ATCC13869 (Miwa et al., Agricultural and Biological Chemistry 48, 2901–2903 (1984)), pX18 from *Brevibacterium lactofermentum* ATCC21086 (Yeh et al, Gene 47, 301–308 (1986)) and pBL1 from *Brevibacterium lactofermentum* ATCC2179B (Santamaria et al., Journal of General Microbiology 130, 2237–2246 (1984)).

The pHM1519 group comprises plasmids pCG1 from *Corynebacterium glutamicum* ATCC31808 (U.S. Pat. No. 4,617,267), pHM1519 from *Corynebacterium glutamicum* ATCC13058 (Miwa et al., Agricultural and Biological Chemistry 48, 2901–2903 (1984)), pSR1 from *Corynebacterium glutamicum* ATCC19223 (Yoshihama et al., Journal of Bacteriology 162, 591–597 (1985)) and pRN3.1 from *Corynebacterium glutamicum* ATCC39269 (U.S. Pat. No. 4,559,308).

In addition to members of these two groups of plasmids, the cryptic plasmids pCG2 from *Corynebacterium glutamicum* ATCC31832 (U.S. Pat. No. 4,489,160) and pAG3 from *Corynebacterium melassecola* 22220 (U.S. Pat. No. 5,158,891) have also been isolated.

The only selection systems which have hitherto been available are two antibiotic resistance markers which were identified on the streptomycin/spectinomycin resistance plasmid pCG4 from *Corynebacterium glutamicum* ATCC31830 (U.S. Pat. No. 4,489,160) and on the tetracycline resistance plasmid pAG1 from *Corynebacterium melassecola* 22243 (U.S. Pat. No. 5,158,891). Plasmid pCG4 also bears the sulII gene which imparts sulfamethoxazole resistance, the sequence of which gene was determined by Nesvera et al. (FEMS Microbiology Letters 169, 391–395 (1998)).

If strains which produce amino acids, vitamins or nucleotides are to be rapidly investigated and improved, it is important to have plasmid vectors which are mutually compatible and are sufficiently stable.

It is known from the prior art that pHM1519 plasmid derivatives and pEL1 plasmid derivatives may coexist. It is furthermore known that the plasmids pGA1 and pGA2 described in U.S. Pat. No. 5,175,108 are compatible. Plasmid vectors having high, moderate or low copy numbers so that expression of the gene under consideration may be graduated are also of significance. Most known plasmids have a high copy number. Only the plasmid pGA2 described in U.S. Pat. No. 5,175,108 is known to have a low copy number.

The widely used plasmid vectors are composed of components originating from the species *C. glutamicum* and components from another species of bacteria, typically *E. coli*. This method introduces foreign DNA into the species *C. glutamicum*. Functional plasmid vectors with a graduated copy number which contain only endogenous DNA and thus meet the criteria of self cloning are not known in specialist circles.

SUMMARY OF THE INVENTION

Object of the Invention

It is an object of the invention to provide novel plasmids that are suitable for constructing plasmid vectors having improved characteristics for coryneform bacteria which produce amino acids, vitamins and nucleotides.

Description of the Invention

Amino acids, vitamins and nucleotides are used in animal nutrition, in the food industry, in the pharmaceuticals industry and in human medicine. These substances are produced with strains of coryneform bacteria. Production characteristics are improved by amplifying suitable genes by means of plasmid vectors. There is accordingly general interest in providing novel plasmid vectors having improved characteristics.

The present invention provides the mutually compatible plasmids pTET3 and pCRY4, isolated from the strain of *Corynebacterium glutamicum* deposited under DSM number 5816, wherein 1.1 plasmid pTET3 is characterised by a length of ~27.8 kbp and the restriction map shown in FIG. 1, and an antibiotic resistance region and 1.2 plasmid pCRY4 is characterised by a length of ~48 kbp and the restriction map shown in FIG. 2.

The present invention also provides composite plasmids of pTET3 and pCRY4 capable of autonomous replication in coryneform bacteria, said plasmids containing 2.1 a part or the entire quantity of the nucleotide sequences 2.2 at least one DNA replication region derived from one of the plasmids pTET3 or pCRY4

2.3 optionally a gene fragment which is derived from a plasmid which can multiply in *E. coli*, *B. subtilis* or Streptomyces and 2.4 at least one region for expressing active substance resistance, preferably from the plasmid pTET3.

The present invention also provides novel composite plasmids that contain at least part of an active substance resistance region.

The novel plasmid pTET3, the restriction map of which is, shown in FIG. 1, has
1. a replication region comprising the nucleotide sequence shown in SEQ ID NO:1 and
2. an antibiotic resistance region consisting of a tetA gene imparting tetracycline resistance and an aadA gene imparting streptomycin and spectinomycin resistance, shown in SEQ ID NO:6.

The novel plasmid pCRY4, the restriction map of which is shown in FIG. 2, has a replication region comprising the nucleotide sequence shown in SEQ ID NO:4.

The present invention also provides the production of amino acids, vitamins and nucleotides using plasmid vectors (composite plasmids) which contain pTET3 and pCRY4 and optionally pGA1 or pGA2 nucleotide sequences.

*Corynebacterium glutamicum* LP-6, which was deposited as DSM5816 in the context of EP-B 0 472 869, contains the novel plasmids pTET3 and pCRY4 in addition to the plasmids pGA1 and pGA2 described therein. The storage period for DSM5816 has been extended pursuant to rule 9.1 of the Budapest Treaty.

Plasmids pTET3 and pCRY4 are prepared by culturing strain LP-6 in a conventional medium, such as for example brain-heart bouillon or Luria-Bertani medium. The cells were harvested by centrifugation, treated with lysozyme and digested by the alkaline lysis method. The DNA is then purified by anion exchange chromatography on silica gel particles, precipitated with ethanol or isopropanol and then resuspended in $H_2O$. Complete systems for isolating plasmid DNA are commercially available as "kits". One example of such a kit is the "NucleoBond Plasmid Kit" from Clonetech Laboratories GmbH. The person skilled in the art will find detailed instructions relating to the use of this kit in the manual "NucleoBond Nucleic Acid Purification Kits and Cartridges, User Manual (PT3167-1)" from Clonetech Laboratories GmbH (Heidelberg, Germany, 1997). Plasmids pTET3 and pCRY4 are revealed as plasmid bands by separating the total plasmid DNA obtained in this manner by agarose gel electrophoresis and staining with ethidium bromide. DNA from the plasmid pTET3 and DNA from the plasmid pCRY4 may then be isolated from the agarose gel. To this end, the agarose gel containing the plasmid DNA is combined with a chaotropic reagent, the plasmid DNA present in the resultant solution is bound onto the surface of glass or silica gel particles and then eluted back out from this matrix. The person skilled in the art will find detailed instructions relating to this process in the manual "QIAEX II Handbook for DNA Extraction from Agarose Gels" from Qiagen GmbH (Hilden, Germany, 1997). In this manner, it is possible to prepare pTET3 DNA and pCRY4 DNA in pure form.

DNA of the plasmid to be investigated is treated with restriction enzymes individually or in combination as described by Roberts et al. (Nucleic Acids Research 27, 312–313 (1999)). The resultant DNA fragments are separated by agarose gel electrophoresis and the restriction sites assigned. The person skilled in the art will find instructions in this connection, for example, in Rodriguez and Tait "Recombinant DNA Techniques: An Introduction" (Addison-Wesley Publishing Company, London, 1983) or in "Guide to Molecular Cloning Techniques" edited by Berger and Kimmel (Methods in Enzymology, Vol. 152, Academic Press, London, 1987). In this manner, the length of the plasmid may be determined or the restriction map plotted. Plasmid pTET3 has a length of approximately 27.8 kbp and is shown in FIG. 1. Plasmid pCRY4 has a length of approximately 48 kbp and is shown in FIG. 2.

Plasmids pTET3 and pCRY4 have a moderate or low copy number. By virtue of this property, they advantageously complement the range of known plasmids for Corynebacterium. Instructions relating to determining copy number may be found, for example, in Miwa et al. (Agricultural and Biological Chemistry 48, 2901–2903 (1984)) and Vohradsky et al. (Electrophoresis 13, 601–612 (1993)).

In order to ensure simple handling of plasmids pTET3 and pCRY4, the DNA region responsible for replication on each plasmid is determined. Known plasmid vectors of *Escherichia coli* such as for example pK18 (Pridmore, Gene 56, 309–312 (1987)), pK18mob2 (Tauch et al., Plasmid 40, 126–139 (1998)) or pCR2.1 (Invitrogen BV, Groningen, Netherlands), which cannot replicate in coryneform bacteria, but the resistance gene of which is expressed, are used for this purpose. DNA from plasmids pTET3 and pCRY4 is isolated and treated with restriction enzymes. Individual DNA fragments obtained in this manner may optionally in turn be isolated. The DNA of the plasmid vectors used is treated with the same restriction enzymes or such enzymes that produce compatible ends. The resultant DNA molecules are mixed and treated with T4 DNA ligase. These "cloning" techniques were known in the prior art and are described in detail in, for example, Sambrook et al. (Molecular Cloning: A Laboratory Manual, Cold Spring Harbor Laboratory Press (1989)). After transforming a coryneform host, for example *Corynebacterium glutamicum*, with the ligation mixture and selecting for the resistance gene of the *E. coli* plasmid vector used, transformants are obtained. Instructions relating to the transformation of coryneform bacteria may be found, for example, in Thierbach et al. (Applied and Environmental Microbiology 29, 356–362 (1988)), in Liebl et al. (FEMS Microbiology Letters 65, 299–304 (1989)) or in Dunican et al. (Bio/Technology 7, 1067–1070 (1989)). The plasmid DNA of these transformants contains DNA segments of pTET3 or pCRY4, which impart the ability to replicate in coryneform bacteria. Examples of these are:

plasmid pTET3-Rep, which consists of the *E. coli* plasmid pK18mob2 and the replication region of plasmid pTET3 (FIG. 3), and plasmid pCRY4-Rep, which consists of the *E. coli* plasmid pK18mob2 and the replication region of plasmid pCRY4 (FIG. 4).

The sections of DNA characterised in this manner are then in turn subcloned into usual vectors suitable for DNA sequencing. Examples of such vectors suitable for DNA sequencing are, for example, the plasmids pGEM-5zf(−) or pGEM-5zf(+) from Promega Corporation (Promega Protocols and Application Guide, Second Edition, 1991, part number Y981, Promega Corporation, Madison, Wis., USA), plasmid pUC19 (Yanish-Perron et al., Gene 33, 103–119 (1985)) or plasmid pK18 (Pridmore, Gene 56, 309–312 (1987)).

DNA sequencing methods are described inter alia in Sanger et al. (Proceedings of the National Academy of Sciences of the United States of America USA, 74, 5463–5467, 1977) and in Zimmermann et al. (Nucleic Acids Research 18, 1067 (1990)).

The resultant DNA sequences may then be investigated using known algorithms or sequence analysis programs, for example the "STADEN computer software package" (Molecular Biotechnology 5, 233–241 (1996)), Butler's GCG program (Methods of Biochemical Analysis 39, 74–97 (1998)), Pearson & Lipman's FASTA algorithm (Proceedings of the National Academy of Sciences USA 85, 2444–2448 (1988)) or Altschul et al.'s BLAST algorithm (Nature Genetics 6, 119–129 (1994)) and compared with the sequence entries available in publicly accessible databases. Publicly accessible nucleotide sequence databases are, for example, the European Molecular Biology Laboratory database (EMBL, Heidelberg, Germany) or the National Center for Biotechnology Information database (NCBI, Bethesda, Md., USA).

The novel DNA sequence responsible for replication of the plasmid pTET3, which sequence is provided by the present invention as SEQ ID NO:1, and which bears the repA gene responsible for replication and the parA gene responsible for stability, was obtained in this manner. The amino acid sequences of the encoded proteins were furthermore deduced from this DNA sequence. SEQ ID NO:2 shows the resultant amino acid sequence of the stabilisation protein ParA, while SEQ ID NO:3 shows the resultant amino acid sequence of the replication protein RepA of pTET3.

The novel DNA sequence responsible for replication of the plasmid pCRY4, which sequence is provided by the present invention as SEQ ID NO:4, and which bears the repA gene responsible for replication of pCRY4, was furthermore obtained in this manner. SEQ ID NO:5 shows the deduced amino acid sequence of the replication protein RepA of plasmid pCRY4.

Few naturally occurring genes that impart resistance to antibiotics in *Corynebacterium glutamicum* are known. The inventors were accordingly all the more surprised to find that plasmid pTET3 imparts resistance to the antibiotics tetracycline, streptomycin, spectinomycin and sulfamethoxazole.

In order to identify antibiotic resistance genes on new plasmids, the strain to be investigated, in the present case Corynebacterium glutamicum LP-6, and a sensitive control strain, in the present case *Corynebacterium glutamicum* ATCC13032, are initially tested for resistance or sensitivity to various antibiotics and concentrations of antibiotics. The National Committee of Clinical Laboratory Standards (NCCLS) experimental procedure is preferably used for this purpose ("Methods for dilution antimicrobial susceptibility tests for bacteria that grow aerobically", fourth edition; Approved Standard, M7-A4, NCCLS 17(2), (1997)). Using the method of "Approved Standard M7-A4", it is possible to determine inhibition concentrations and thus to ascertain the resistance of the investigated strain of bacteria.

The plasmid to be investigated, in the present case pTET3, is then isolated from strain LP-6 as described above and used to transform a suitable control or indicator strain, in the present case strain ATCC13032. Methods for transforming coryneform bacteria are described, for example, in Thierbach et al. (Applied and Environmental Microbiology 29, 356–362 (1988)), in Liebl et al. (FEMS Microbiology Letters 65, 299–304 (1989)) or in Dunican et al. (Bio/Technology 7, 1067–1070 (1989)). Selection is performed on conventional, complex nutrient media, such as for example brain-heart bouillon or Luria-Bertani medium, which are supplemented with the appropriate antibiotics. The antibiotic and the concentration thereof for this selection process is determined on the basis of the above-mentioned "Approved Standard, M7-A4". In this manner, strain ATCC13032[pTET3], is obtained by selection for tetracycline resistance. The resistance/sensitivity of strain ATCC13032[pTET3]) and of the control strain ATCC13032 is then investigated using the above-mentioned method, yielding the result that strain ATCC13032[pTET3] is resistant to the antibiotics tetracycline, streptomycin, spectinomycin and sulfamethoxazole.

This antibiotic resistance was further characterised by cloning and sequencing. To this end, plasmid pTET3 is isolated from strain LP-3 or ATCC13032[pTET3], treated with suitable restriction enzymes, mixed with cloning vectors treated in the same manner and treated with T4 DNA ligase. The ligation mixture is transferred by transformation into a suitable cloning host of *Escherichia coli*. Selection for transformants is performed on a complex nutrient medium, which is supplemented with the appropriate antibiotic. The person skilled in the art will find instructions relating to this method in Sambrook et al. Examples of suitable cloning vectors are pUC19 (Yanish-Perron et al., Gene 33, 103–119 (1985)), pK18mob2 (Tauch et al., Plasmid 40, 126–139 (1998)) or pCR2.1 (Invitrogen BV, Groningen, Netherlands). Suitable hosts are in particular those *E. coli* strains with restriction and recombination defects. One example of such a strain is the strain DH5αMCR, which has been described by Grant et al. (Proceedings of the National Academy of Sciences USA, 87, 4645–4649 (1990)). Transformation methods are described, for example, in Hanahan (Journal of Molecular Biology 166, 577–580 (1983)) or Tauch et al. (Plasmid 40, 126–139 (1998)). Transformant selection is performed by using the antibiotics to which plasmid pTET3 imparts resistance. The plasmid DNA of the resultant transformants is then isolated and the cloned DNA fragments of plasmid pTET3 are sequenced. The sequences are then analysed as described above and compared with databases of collected DNA sequences.

The inventors discovered in this manner that the genes which impart resistance to the antibiotics tetracycline, streptomycin, spectinomycin and sulfamethoxazole are located on a continuous DNA fragment. This DNA fragment is shown as a restriction map in FIG. 5. The DNA portion containing the genes tetR, tetA and aadA is shown as a sequence in SEQ ID NO:6 and is provided by the invention.

The amino acid sequences of the protein encoded by the particular gene were furthermore deduced from the ascertained DNA sequence. SEQ ID NO:7 shows the deduced amino acid sequence of the tetracycline resistance protein TetA encoded by the tetA gene and SEQ ID NO:8 shows the deduced amino acid sequence of the spectinomycin/streptomycin resistance protein aadA encoded by the aadA gene. SEQ ID NO:9 shows the coding region of the tetR gene and SEQ ID NO:10 the amino acid sequence of the tetracycline resistance repressor protein TetR.

Coding DNA sequences arising from SEQ ID NO:6 based on the degeneracy of the genetic code are also provided by the present invention. DNA sequences which hybridise with SEQ ID NO:1 or parts of SEQ ID NO:1 are similarly provided by the invention. Conservative substitutions of amino acids in proteins, for example the substitution of glycine for alanine or of aspartic acid for glutamic acid, are known to those of skill in the art as "sense mutations", which result in no fundamental change in activity of the protein, i.e. they are functionally neutral. Amino acid sequences arising in a corresponding manner from SEQ ID NOS:7, 8 and 10 are also provided by the present invention.

The DNA fragments of plasmids pTET3 and pCRY4 from *Corynebacterium glutamicum* strain LP-6 may then be combined with DNA fragments of known plasmids of other microorganisms, such as for example *Escherichia coli* or *Corynebacterium glutamicum*, to yield further, novel plasmid vectors. For the purposes of the present invention, it is preferred to use plasmid DNA from other strains of the species *Corynebacterium glutamicum*. This approach, known as self cloning, has the advantage that no foreign nucleotide sequences are introduced in the species *Corynebacterium glutamicum*. Such further developed plasmid vectors may consist solely of constituents of the novel plasmid pTET3, i.e. of a replication region and at least one antibiotic resistance region, which is used as a selection marker. One example of such a vector is the plasmid vector pSELF3-1 shown in FIG. 6. These vectors may, however, also be composed of constituents of a known plasmid and constituents of pTET3 or pCRY4. One example of such a vector is the plasmid vector pSELF1-1 shown in FIG. 7, in which the known cryptic plasmid PGA1 (U.S. Pat. No. 5,175,108) has been provided with the tetA gene which imparts tetracycline resistance of pTET3.

The plasmid vectors constructed from the novel plasmids pTET3 and pCRY4 may advantageously be used for the fermentative production of industrially interesting metabolites such as amino acids, vitamins and nucleotides.

For example, within the framework of the present invention, a lysC(FER) allele of *C. glutamicum* which encodes a feed-back resistant aspartate kinase was cloned into *C. glutamicum* ATCC13032 by means of pSELF1-1. In this manner, a self-cloned lysine producing strain of *C. glutamicum* was produced.

By way of further example, the panD gene coding for aspartate α-decarboxylase from *C. glutamicum* was cloned into the *C. glutamicum* strain ATCC13032ΔilvA by means of pSELF1-1. In this manner, a self-cloned pantothenic acid producing strain of *C. glutamicum* was produced.

One very particular advantage of the novel plasmids pTET3 and pCRY4 and further plasmid vectors based thereon is that they exhibit an unusually high level of compatibility with known plasmids or plasmid vectors.

It was thus found that plasmid pTET3 may coexist in the presence of or is compatible with plasmid vectors based on pGA1 (U.S. Pat. No. 5,175,108), pAG3 (U.S. Pat. No. 5,158,891), pBL1 (Santamaria et al., Journal of General Microbiology 130, 2237–2246 (1984)) or on pHM1519 (Miwa et al., Agricultural and Biological Chemistry 48, 2901–2903 (1984)). This compatibility of pTET3 is still retained when the host cell concerned already contains two or more known plasmid vectors, for example a pBL1 derivative and simultaneously a pHM1519 derivative. pTET3's capacity to coexist with known plasmids or plasmid vectors is ensured over a sufficiently long period of time or for a sufficiently large number of generations.

It has furthermore been found that plasmid pCRY4 may coexist in the simultaneous presence of or is compatible with plasmids pTET3, pGA1 (U.S. Pat. No. 5,175,108) and pGA2 (U.S. Pat. No. 5,175,108) in the presence of plasmid vectors based on pAG3 (U.S. Pat. No. 5,158,891), pBL1 (Santamaria et al., Journal of General Microbiology 130, 2237–2246 (1984)) or on pHM1519 (Miwa et al., Agricultural and Biological Chemistry 48, 2901–2903 (1984)). This compatibility of pCRY3 is still retained when the host cell concerned already contains two or more known plasmid vectors, for example a pBL1 derivative and simultaneously a pHM1519 derivative. pCRY4's capacity to coexist with known plasmids or plasmid vectors is ensured over a sufficiently long period of time or for a sufficiently large number of generations.

The improved compatibility of plasmids pTET3 and pCRY4 may advantageously be used for improving strains which produce amino acids, vitamins and nucleotides. Sahm and Eggeling (Applied and Environmental Microbiology 65, 1973–1979 (1999)) thus describe the pantothenic acid producing strain ATCC13032ΔilvA [pECM3ilvBNCD, pEKEx2panBC]. This strain bears the pHM1519 derivative pECM3ilvBNCD and the pBL1 derivative pEKEx2panBC. It proved possible to achieve a distinct improvement in the performance characteristics of the stated strain, which already contains two plasmids, after transferring the panD gene by means of the plasmid vector pSELF3-1.

Figure 1:
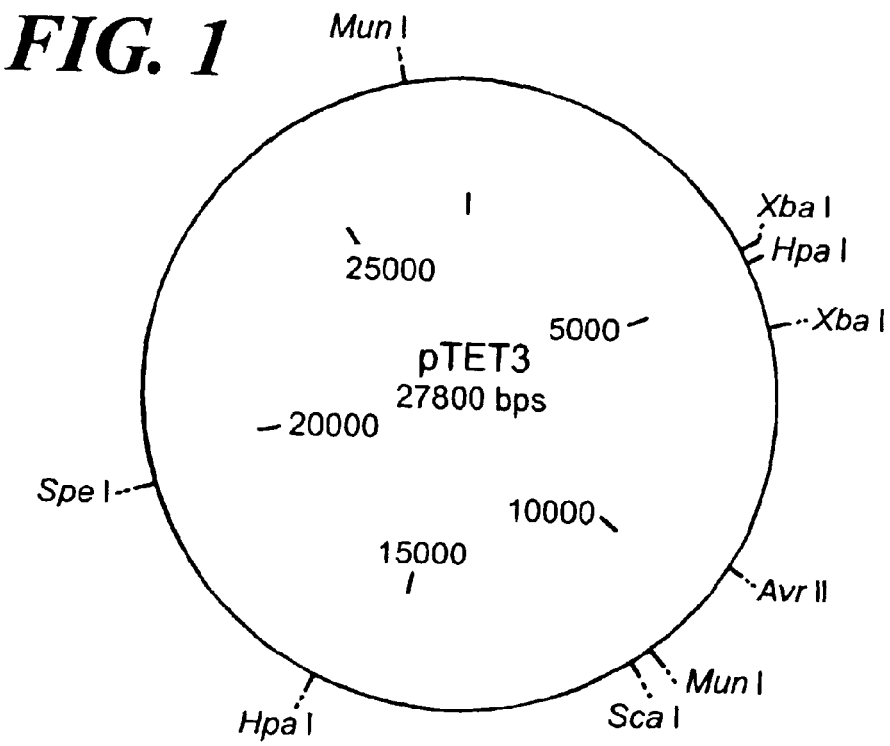
FIG. 1: Restriction map of plasmid pTET3.

The lengths stated should be considered to be approximate. The abbreviations and terms used have the following meaning:

bps: Base pairs
AvrII: Restriction site for restriction enzyme AvrII
ClaI: Restriction site for restriction enzyme ClaI
EcoRI: Restriction site for restriction enzyme EcoRI
EcoRV: Restriction site for restriction enzyme EcoRV
FspI: Restriction site for restriction enzyme FspI
HindIII: Restriction site for restriction enzyme HindIII
HpaI: Restriction site for restriction enzyme HpaI
MunI: Restriction site for restriction enzyme MunI
NruI: Restriction site for restriction enzyme NruI
PstI: Restriction site for restriction enzyme PstI
SacI: Restriction site for restriction enzyme SacI
SalI: Restriction site for restriction enzyme SalI
SalI: Restriction site for restriction enzyme SalI
ScaI: Restriction site for restriction enzyme ScaI
SmaI: Restriction site for restriction enzyme SmaI
SpeI: Restriction site for restriction enzyme SpeI
SphI: Restriction site for restriction enzyme SphI
XbaI: Restriction site for restriction enzyme XbaI
XhoI: Restriction site for restriction enzyme XhoI
aadA: Gene for spectinomycin/streptomycin resistance protein
parA: Gene for stabilisation protein ParA
sulI: Gene for the sulfamethoxazole resistance protein
repA: Gene for the replication protein RepA
tetA: Gene for the tetracycline resistance protein
tetR: Gene for the tetracycline repressor protein

DETAILED DESCRIPTION OF THE INVENTION

The present invention is illustrated in greater detail by the following practical examples.

The following strains of bacteria were used:

*Corynebacterium glutamicum* LP-6 was deposited in the context of EP-B 0 472 869 with Deutsche Sammlung fur Mikroorganismen und Zellkulturen (DSMZ, Braunschweig, Germany) under number DSM5816. The storage period for DSMS816 has been extended pursuant to rule 9.1 of the Budapest Treaty. DSM5816 has the following taxonomic features:

Cell shape: Y-shaped branching
Peptidoglycan: meso-diaminopimelic acid

Mycolic acids: *Corynebacterium* mycolic acids with a high level of similarity to DSM20300

Fatty acid pattern: fatty acid pattern typical of Corynebacterium with unbranched, saturated and unsaturated fatty acids with a high level of similarity to DSM20300.

G+C content: 55.1%

16S rDNA sequence: 98.6% identical in comparison with DSM20300

DNA-DNA homology: 81.6% to DSM20300

*Corynebacterium glutamicum* ATCC13032 was obtained from the American Type Culture Collection (Manassas, USA).

*Corynebacterium glutamicum* ATCC13032ΔivA is deposited with Deutsche Sammlung für Mikroorganismen und Zellkulturen (DSMZ, Braunschweig, Germany) under number DSM12455.

The general genetic methods stated and the nutrient media used in the following Examples are described in Sambrook et al. (Molecular Cloning: A Laboratory Manual, Cold Spring Harbor Laboratory Press (1989)). Electrically-assisted transfer of plasmid DNA was performed using the method of Liebl et al. (FEMS Microbiology Letters 65, 299–304 (1989)).

The DNA fragments described in the following Examples were sequenced in accordance with the dideoxy chain termination method according to Sanger et al. (Proceedings of the National Academy of Sciences USA 74, 5463–5467 (1977)). The resultant raw sequence data were processed using the "STADEN software package" (Staden, Molecular Biotechnology 5, 233–241 (1996)). Computer-aided coding range analysis was performed using XNIP software (Staden, Molecular Biotechnology 5, 233–241 (1996)). Further sequence analysis was performed using the "BLAST programs" (Altschul et al., Nucleic Acids Research 25, 3389–3402 (1997)).

EXAMPLE 1

Isolation and Characterisation of the Novel Plasmids pTET3 and pCRY4

In order to identify novel plasmids and isolate plasmid DNA, the bacterial strain *Corynebacterium glutamicum* LP-6 was cultured in LB medium and isolated in accordance with the instructions given in "NucleoBond Nucleic Acid Purification Kits and Cartridges User Manual (PT3167-1)" (Clonetech Laboratories GmbH, Heidelberg, Germany, 1997). The isolated plasmid DNA was separated in a 0.8% agarose gel and the plasmid bands corresponding to the novel plasmids pTET3 and pCRY4 were each reisolated separately from the agarose gel. The experimental procedure was in accordance with "QIAEX II Handbook for DNA Extraction from Agarose Gels" (Qiagen GmbH, Hilden, Germany, 1997). The reisolated plasmid DNA of pTET3 was then digested in accordance with the manufacturers' instructions with the restriction enzymes AvrII, MunI (New England Biolabs GmbH, Schwalbach, Germany), HpaI, ScaI, XbaI (Pharmacia Biotech Europe GmbH, Freiburg, Germany) and SpeI (Roche Diagnostics GmbH, Mannheim, Germany) in each case individually and in combination. The restriction batches were then separated in a 0.8% agarose gel. By comparing the resultant DNA fragments with DNA fragments of known length (DNA Molecular Weight Marker X, Roche Diagnostics GmbH, Mannheim, Germany), the restriction map of plasmid pTET3 from *Corynebacterium glutamicum* LP-6 shown in FIG. 1 was determined.

Figure 2:
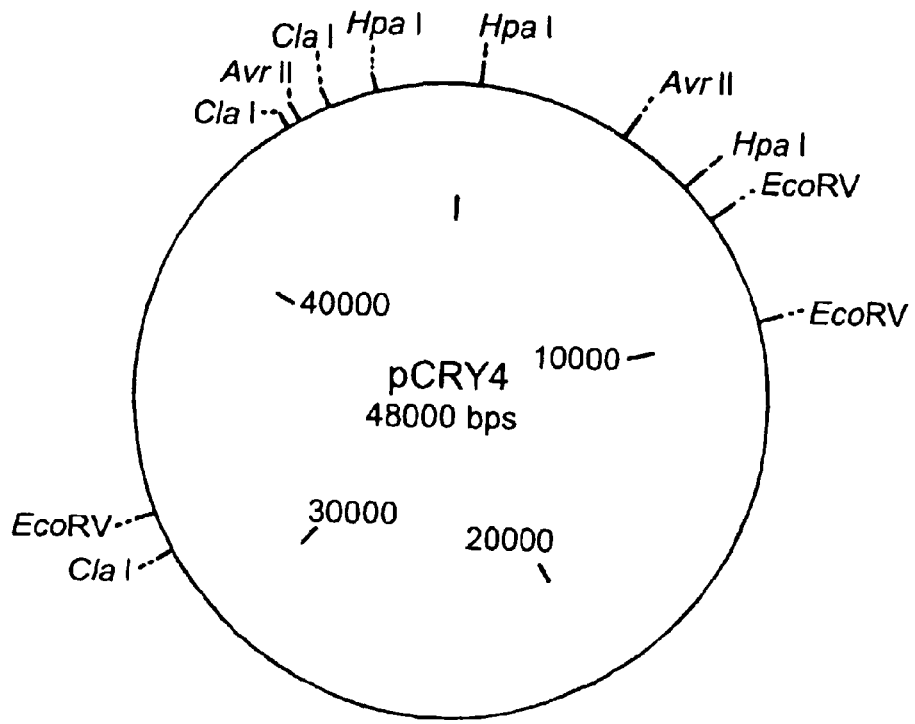
FIG. 2: Restriction map of plasmid pCRY4.

The reisolated plasmid DNA of the novel plasmid pCRY4 from *Corynebacterium glutamicum* LP-6 was then digested in accordance with the manufacturers' instructions with the restriction enzymes AvrII (New England Biolabs GmbH, Schwalbach, Germany), EcoRV, HpaI and ClaI (Pharmacia Biotech Europe GmbR, Freiburg, Germany) in each case individually and in combination. The restriction batches were then separated in a 0.8% agarose gel. By comparing the resultant DNA fragments with DNA fragments of known length (DNA Molecular Weight Marker X, Roche Diagnostics GmbH, Mannheim, Germany), the restriction map of plasmid pCRY4 from *Corynebacterium glutamicum* LP-6 shown in FIG. 2 was determined.

EXAMPLE 2

Isolation and Sequencing of the Replication Region of Plasmid pTET3

In order to isolate a DNA region which is required for stable replication of the novel plasmids in coryneform bacteria, plasmid DNA was initially isolated from *Corynebacterium glutamicum* LP-6 by alkaline treatment of the bacterial cells. The experimental method is described in detail in the instructions for "NucleoBond Nucleic Acid Purification Kits and Cartridges User Manual (PT3167-1)" (Clonetech Laboratories GmbH, Heidelberg, Germany, 1997). The resultant DNA preparation of *Corynebacterium glutamicum LP*-6 was then separated in a 0.8% agarose gel and investigated for the presence of plasmid bands. The identified plasmid bands from *Corynebacterium glutamicum* LP-6 were assigned to the known plasmids pGA1 and pGA2 (U.S. Pat. No. 5,175,108) and the novel plasmids pTET3 and pCRY4. The plasmid bands corresponding to the plasmid pTET3 were reisolated from the agarose gel (c.f. Example 1). The experimental procedure may be found in "QIAEX II Handbook for DNA Extraction from Agarose Gels" (Qiagen GmbH, Hilden, Germany, 1997). The reisolated plasmid DNA was then digested with the restriction enzymes AvrII (New England Biolabs GmbH, Schwalbach, Germany) and HpaI (Pharmacia Biotech Europe GmbH, Freiburg, Germany) and cloned into the vector pK18mob2 (Tauch et al., Plasmid 40, 126–139 (1998)) which had been cut with the restriction enzymes XbaI and SmaI (Pharmacia Biotech Europe GmbH, Freiburg, Germany). DNA restriction and DNA ligation using the enzyme T4 DNA ligase (Roche Diagnostics GmbH, Mannheim, Germany) were performed in accordance with the manufacturer's instructions. This ligation mixture was then electroporated into strain *Corynebacterium glutamicum* ATCC13032. Selection was performed on LB agar containing 25 μg/ml of kanamycin. After 48 hours' incubation at 30° C., colonies were isolated which contained plasmids. The presence of plasmids in the transformed bacterial cells was shown using an alkaline lysis method in accordance with the instructions in "QIAGEN Plasmid Mini Handbook for Plasmid Mini Kit" (Qiagen GmbH, Hilden, Germany, 1997). The isolated plasmid was named pTET3-Rep. Restriction analysis of pTET3-Rep and a comparison of the fragment lengths obtained with DNA fragments of known length (DNA Molecular Weight Marker X, Roche Diagnostics GmbH, Mannheim, Germany) revealed that pTET3-Rep consists of the cloning vector pK18mob2, which contains a DNA fragment from pTET3 of an approximate size of 4500 base pairs (bp).

Figure 3:
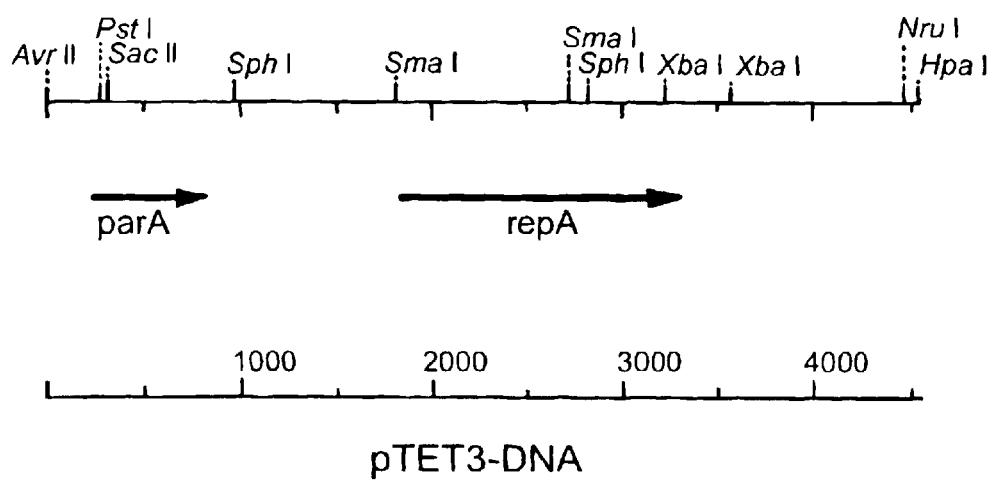
FIG. 3: Map of replication region of plasmid pTET3.

For the purposes of double-stranded DNA sequencing of the approximately 4500 bp DNA fragment from pTET3-Rep, the DNA was isolated in accordance with the instructions of "NucleoBond Nucleic Acid Purification Kits and Cartridges User Manual (PT3167-1)" (Clonetech Laboratories GmbH, Heidelberg, Germany, 1997). Sequencing and subsequent coding region analysis revealed two open reading frames (ORFs) on the sequenced DNA fragment. FIG. 3 shows a restriction map of the sequenced DNA fragment of pTET3-Rep, which also indicates the position of the two identified ORFs. Analysis with the BLAST programs revealed that ORF1 encodes a stabilisation protein designated as ParA and that ORF2 encodes a replication protein designated as RepA. ORF1 was accordingly designated as the parA gene and ORF2 as the repA gene. The DNA sequence of the cloned fragment is set forth in SEQ ID NO:1. The amino acid sequence of the stabilisation protein ParA, deduced from the DNA sequence, is set forth in SEQ ID no. 2 and the deduced amino acid sequence of the replication protein RepA is set forth in SEQ ID NO:3.

EXAMPLE 3

Determination of the Copy Number of the pTET3 Replicon in Corynebacterium glutamicum ATCC13032

In order to determine the copy number of plasmid pTET3-Rep, the bacterial strain Corynebacterium glutamicum ATCC13032 [pTET3-Rep] was cultured for 20 hours at 30° C. in 100 ml of LB medium with 25 µg/ml of kanamycin. The total DNA of the strain was then isolated from 25 ml of bacterial culture using the method according to Tauch et al. (Plasmid 34, 119–131 (1995)). The resultant DNA was treated for 20 minutes at 37° C. with 20 µg/ml of RNase/DNase-free (Roche Diagnostics GmbH, Mannheim, Germany) and, after phenol extraction, separated electrophoretically in 0.8% agarose gel. The agarose gel stained with ethidium bromide was photographed under UV light with a Cybertech CS1 camera system (Cybertech GmbH, Berlin, Germany) and the negative image was digitised with an HP Scanjet 6100 C/T Optical Scanner (Hewlett-Packard Co., Palo Alto, Calif., USA). The band density of the DNA was quantified densitometrically using the Wincam computer system from Cybertech GmbH (Berlin, Germany). The copy number was calculated in accordance with the method of Miwa et al. (Agricultural and Biological Chemistry 48, 2901–2903 (1984)) assuming a chromosome size of 3082 kb (Bathe et al., Molecular and General Genetics 252, 255–265 (1996)) and revealed a value of 15 plasmids per chromosome for plasmid pTET3-Rep in Corynebacterium glutamicum ATCC13032.

EXAMPLE 4

Isolation and Sequencing of the Replication Region of Plasmid pCRY4

In order to isolate the DNA region which is required for stable replication of the novel plasmid pCRY4 in coryneform bacteria, plasmid DNA was initially isolated from Corynebacterium glutamicum LP-6 by alkaline treatment of the bacterial cells. The experimental method may be found in the instructions for "NucleoBond Nucleic Acid Purification Kits and Cartridges User Manual (PT3167-1)" (Clonetech Laboratories GmbH, Heidelberg, Germany, 1997). The resultant DNA preparation of Corynebacterium glutamicum LP-6 was then separated in a 0.8 agarose gel and investigated for the presence of a pCRY4 plasmid band. The identified plasmid band corresponding to the novel plasmid pCRY4 was then reisolated from the agarose gel (c.f. Example 1). The experimental procedure may be found in "QIAEX II Handbook for DNA Extraction from Agarose Gels" (Qiagen GmbH, Hilden, Germany, 1997). The reisolated plasmid DNA was then digested with the restriction enzyme SphI (Pharmacia Biotech Europe GmbH, Freiburg, Germany) and cloned into the vector pK18mob2 (Tauch et al., Plasmid 40, 126–139 (1998)) which had been cut with the restriction enzyme SphI. DNA restriction and DNA ligation using the enzyme T4 DNA ligase (Roche Diagnostics GmbH, Mannheim, Germany) were performed in accordance with the manufacturer's instructions. The ligation mixture was then transferred with electrical assistance into the coryneform bacterial strain Corynebacterium glutamicum ATCC13032. Selection was performed on LB agar containing 25 µg/ml of kanamycin. After 48 hours' incubation at 30° C., colonies containing plasmids were isolated. The presence of plasmids in the transformed bacterial cells was demonstrated by an alkaline lysis method in accordance with the instructions in "QIAGEN Plasmid Mini Handbook for Plasmid Mini Kit" (Qiagen GmbH, Hilden, Germany, 1997). The isolated plasmid was named pCRY4-Rep. Restriction analysis of pCRY4-Rep and a comparison of the fragment lengths obtained with DNA fragments of known length (DNA Molecular Weight Marker X, Roche Diagnostics GmbH, Mannheim, Germany) revealed that pCRY4-Rep contains an approximately 1900 bp DNA fragment.

Figure 4:
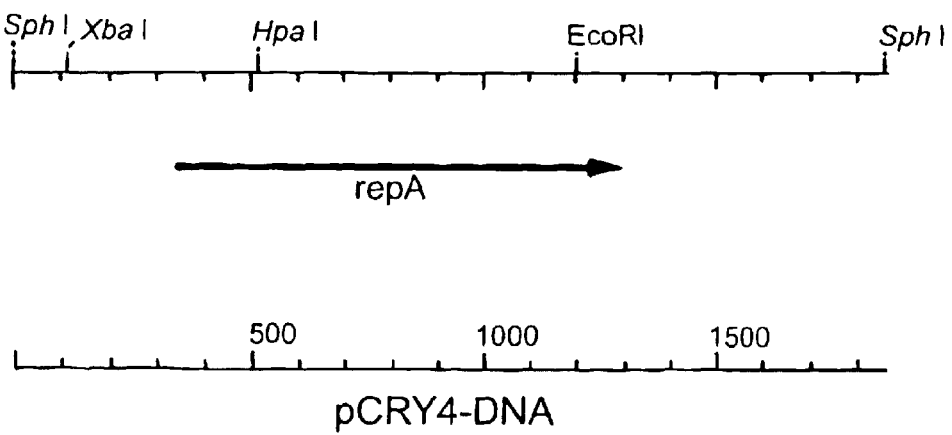
FIG. 4: Map of replication region of plasmid pCRY4

For the purposes of double-stranded DNA sequencing of the approximately 1900 bp DNA fragment from pCRY4-Rep, the DNA was isolated in accordance with the instructions of "NucleoBond Nucleic Acid Purification Kits and Cartridges User Manual (PT3167-1)" (Clonetech Laboratories GmbH, Heidelberg, Germany, 1997). DNA sequencing and computer-aided coding region analysis allowed an open reading frame (ORF1) to be identified on the sequenced DNA fragment. FIG. 4 shows the restriction map of the sequenced DNA fragment of pCRY4-Rep, which also indicates the position of the identified ORF. Analysis with the BLAST programs revealed that ORF1 encodes a replication protein (RepA), which was designated as the repA gene. The DNA sequence of the cloned fragment is reproduced as SEQ ID NO:4, while the deduced amino acid sequence of the replication protein RepA shown in SEQ ID NO:5.

EXAMPLE 5

Determination of the Copy Number of the pCRY4 Replicon in Corynebacterium glutamicum ATCC13032

In order to determine the copy number of plasmid pCRY4-Rep, the bacterial strain Corynebacterium glutamicum ATCC13032 [pCRY4-Rep] was cultured for 20 hours at 30° C. in 100 ml of LB medium with 25 µg/ml of kanamycin. The total DNA of the strain was then isolated from 25 ml of bacterial culture using the method according to Tauch et al. (Plasmid 34, 119–131 (1995)). The resultant DNA was treated for 20 minutes at 37° C. with 20 µg/ml of RNase/DNase-free (Roche Diagnostics GmbH, Mannheim, Germany) and, after phenol extraction, separated electrophoretically in 0.8% agarose gel. The agarose gel stained with ethidium bromide was photographed under UV light with a Cybertech CS1 camera system (Cybertech GmbH, Berlin, Germany) and the negative image was digitised with an HP Scanjet 6100 C/T Optical Scanner (Hewlett-Packard Co., Palo Alto, Calif., USA). The band density of the DNA was quantified densitometrically using the Wincam computer system from Cybertech GmbH (Berlin, Germany). The copy number was calculated in accordance with the method of Miwa et al. (Agricultural and Biological Chemistry 48, 2901–2903 (1984)) assuming a chromosome size of 3082 kb (Bathe et al., Molecular and General Genetics 252, 255–265 (1996)) and revealed a value of 3 plasmids per chromosome for plasmid pCRY4-Rep in Corynebacterium glutamicum ATCC13032.

EXAMPLE 6

Isolation and Sequencing of the Antibiotic Resistance Region of Plasmid pTET3

In order to identify antibiotic resistance regions on the novel plasmids pTET3 or pCRY4, the resistant test strain *Corynebacterium glutamicum* LP-6 and the sensitive control strain *Corynebacterium glutamicum* ATCC13032 were initially cultured in the presence and absence of various antibiotics and antibiotic concentrations in accordance with the experimental method of the National Committee of Clinical Laboratory Standards (National Committee of Clinical Laboratory Standards, Methods for dilution antimicrobial susceptibility tests for bacteria that grow aerobically; Approved Standard, M7-A4 (1997)). The antibiotics required for this test, inter alia the antibiotics tetracycline, spectinomycin, streptomycin and sulfamethoxazole, were obtained from Sigma-Aldrich Chemie GmbH (Deisenhofen, Germany) and used in the concentrations stated in "Approved Standard M7-A4". The nutrient medium required for this test, "MÖLLER-HINTON bouillon" was obtained from Merck KGaA (Darmstadt, Germany) and used in accordance with the manufacturer's instructions. Using the method of "Approved Standard M7-A4", it is possible to determine inhibition concentrations (Table 1) and to identify the resistance of the bacterial strain *Corynebacterium glutamicum* LP-6 to the antibiotics tetracycline, spectinomycin, streptomycin and sulfamethoxazole. Plasmid DNA isolated from *Corynebacterium glutamicum* LP-6 using an alkaline lysis method ("NucleoBond Nucleic Acid Purification Kits and Cartridges User Manual (PT3167-1)", Clonetech Laboratories GmbH, Heidelberg, Germany, 1997) was then transferred with electrical assistance into *Corynebacterium glutamicum* ATCC13032. Selection was performed directly for the presence of the identified tetracycline resistance in the primary selection on LB agar containing 5 µg/ml of tetracycline. The presence of a plasmid in the transformed bacterial strain *Corynebacterium glutamicum* ATCC13032 was then demonstrated by an alkaline lysis method ("NucleoBond Nucleic Acid Purification Kits and Cartridges User Manual (PT3167-1)", Clonetech Laboratories GmbH, Heidelberg, Germany, 1997). Restriction analysis of the isolated plasmid DNA and comparison of the resultant fragment lengths with DNA fragments of known length (DNA Molecular Weight Marker X, Roche Diagnostics GmbH, Mannheim, Germany) and with DNA fragments of plasmid pTET3 revealed that the transformed plasmid which imparts tetracycline resistance is the plasmid pTET3. The transformed strain was named *Corynebacterium glutamicum* ATCC13032 [pTET3].

Another resistance test with the isolated, resistant test strain *Corynebacterium glutamicum* ATCC13032 [pTET3] and the sensitive control strain *Corynebacterium glutamicum* ATCC13032 in accordance with the instructions of the National Committee of Clinical Laboratory Standards in the presence of various concentrations of the antibiotics tetracycline, spectinomycin, streptomycin and sulfamethoxazole demonstrated that the test strain *Corynebacterium glutamicum* ATCC13032 [pTET3] is resistant to these antibiotics (Table 1).

TABLE 1

Minimum inhibition concentration (µg of antibiotic per ml) of various *Corynebacterium glutamicum* strains

| Antibiotic | ATCC13032 | LP-6 | ATCC13032 [pTET3] |
|---|---|---|---|
| Tetracycline | ≦0.75 | ≦12 | ≦12 |
| Spectinomycin | ≦50 | >2000 | >2000 |
| Streptotmycin | ≦0.5 | ≦100 | ≦100 |
| Sulfamethoxazole | ≦150 | ≦300 | ≦300 |

The symbols are defined as follows:
>: The minimum inhibition concentration is greater than the stated value.
≦: The minimum inhibition concentration is less than or equal to the stated value.

The antibiotic resistance of pTET3 was further characterised by reisolating the plasmid DNA from *Corynebacterium glutamicum* ATCC13032 [pTET3] using an alkaline lysis method ("NucleoBond Nucleic Acid Purification Kits and Cartridges User Manual (PT3167-1)", Clonetech Laboratories GmbH, Heidelberg, Germany, 1997). The plasmid DNA was then cleaved with the restriction enzymes HindIII or SacI (Pharmacia Biotech Europe GmbH, Freiburg, Germany) and ligated into the *Escherichia coli* cloning vectors pK18mob2 (Tauch et al., Plasmid 40, 126–139 (1998)) or pUV19 (Pharmacia Biotech Europe GmbH, Freiburg, Germany). DNA restriction and DNA ligation using the enzyme T4 DNA ligase (Roche Diagnostics GmbH, Mannheim, Germany) were performed in accordance with the manufacturer's instructions. The ligation batch was then electroporated into the bacterial strain *Escherichia coli* DH5αMCR (Tauch et al., FEMS Microbiology Letters 123, 343–348 (1994)). After selection on LB agar containing 5 µg/ml of tetracycline or 250 µg/ml of spectinomycin, transformed colonies were obtained, the plasmid vectors of which contained sections of DNA from plasmid pTET3. The presence of plasmids vectors was proven by an alkaline lysis method ("QIAGEN Plasmid Miniprep Handbook for Plasmid DNA", Qiagen GmbH, Hilden, Germany, 1997). Restriction analysis of the isolated plasmid DNA and comparison of the resultant fragment lengths with DNA fragments of known length revealed that the isolated plasmid named pTET3-H9 consists of the plasmid vector pK18mob2 and an approximately 4000 bp DNA fragment from pTET3, and that the isolated plasmid named pXCS10 consists of the plasmid vector pUC19 (Pharmacia Biotech Europe GmbH, Freiburg, Germany) and an approximately 6750 bp DNA fragment from pTET3. The plasmid vector pTET3-H9 obtained from cloning with the restriction enzyme HindIII, imparts tetracycline resistance (5 µg/ml) in *Escherichia coli* DH5αMCR, while the plasmid vector pXCS10 obtained from cloning with the restriction enzyme SacI imparts resistance to the antibiotics spectinomycin (250 µg/ml), streptomycin (250 µg/ml) and sulfamethoxazole (300 µg/ml). A comparison of the restriction analyses of the cloned DNA fragments of pTET3 in plasmid vectors pTET3-H9 and pXCS10 moreover demonstrated that both DNA fragments overlap by approximately 2400 bp and may thus be combined into a continuous DNA strand of a length of approximately 8350 bp.

Figure 5:
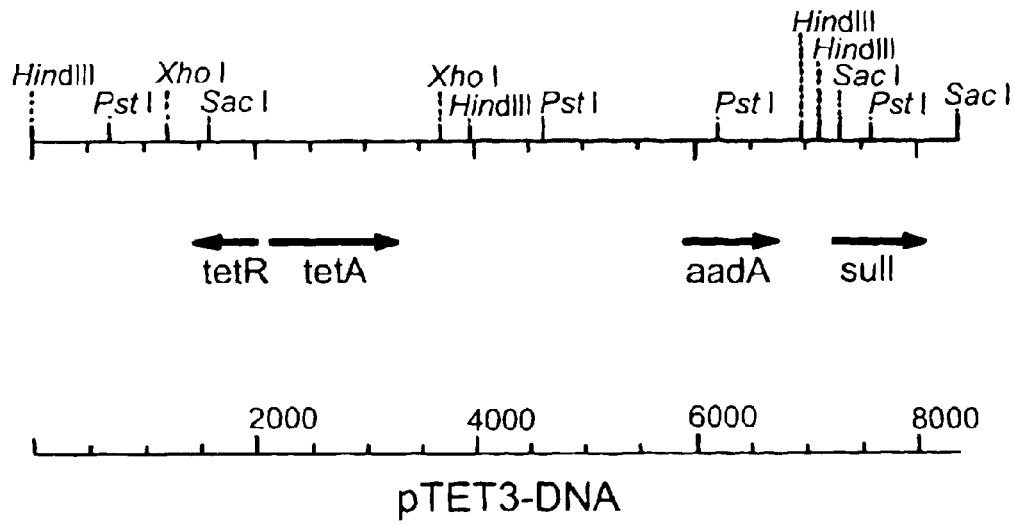
FIG. 5: Map of antibiotic resistance region of plasmid pTET3.

For the purposes of double-stranded DNA sequencing of a continuous, approximately 7300 bp DNA fragment from pTET3 which imparts resistance to tetracycline, spectinomycin and streptomycin, DNA was isolated from plasmids pTET3-H9 and pXCS10 in accordance with the instructions of "QIAprep Miniprep Handbook for Purification of Plasmid DNA" (Qiagen GmbH, Hilden, Germany, 1997). After sequencing and sequence analysis, four open reading frames (ORFs) could be determined on the sequenced DNA fragment. FIG. 5 shows a restriction map of the sequenced DNA region of pTET3 and the position of the identified open reading frames (ORFs). Analysis revealed that ORF1 represents a tetR gene which encodes a tetracycline resistance repressor protein (TetR), ORF2 represents a tetA gene which encodes a tetracycline resistance protein (TetA), ORF3 represents an aadA gene which encodes a spectinomycin/ streptomycin resistance protein (AadA) and ORF4 represents a sulI gene which encodes a sulfamethoxazole resistance protein (SulI). The DNA sequence of the resistance region of pTET3 is reproduced in SEQ ID NO:6. The amino acid sequence of the tetracycline resistance protein (TetA), deduced from the sequence data, is shown in SEQ ID NO:7 and the amino acid sequence of the spectinomycin/ streptomycin resistance protein (AadA), deduced from the sequence data, is shown in SEQ ID NO:8. The coding region of the tetR gene which encodes the tetracycline resistance repressor protein (TetR) is also shown in SEQ ID NO:9 and the deduced amino acid sequence in SEQ ID NO:10.

EXAMPLE 7

Coexistence of Plasmid pTET3 with Known Coryneform Plasmids in *Corynebacterium glutamicum* ATCC13032

The bacterial strain *Corynebacterium glutamicum* ATCC13032 [pTET3] produced in Example 6 was used to analyse the coexistence of the novel plasmid pTET3 from *Corynebacterium glutamicum* LP-6 with known coryneform plasmids.

Electrocompetent cells of this strain were produced, into which plasmid vectors consisting of known plasmids of coryneform bacteria and selection marker fractions were transferred. Plasmid vectors pGA1-KE12, pAG3-Xba, pEBM2 (Tauch et al., Archives of Microbiology 169, 303–312 (1998)), pECM2 (Tauch et al., FEMS Microbiology Letters 123, 343–348 (1994)) and pECM3 were selected for this DNA transfer. Plasmid pGA1-KE12 is an EcoRI fusion of the cryptic plasmid pGA1 from *Corynebacterium glutamicum* LP-6 with vector pK18mob2 (Tauch et al., Plasmid 40, 126–139 (1998)). Plasmid pAG3-Xba is an XbaI fusion of pAG3 and pK18mob2. Plasmid pECM3 is a BamHI-BglII deletion of pECM2. Once transfer of the plasmid vectors pGA1-KE12 (pGA1 derivative), pAG3-Xba (pAG3 derivative), pEBM2 (pBL1 derivative) and pECM2 (pHM1519 derivative), which impart kanamycin resistance, was complete, selection was performed on LB agar containing 25 µg/ml of kanamycin. Plasmid pECM3, a pHM1519 derivative, which imparts chloramphenicol resistance, was additionally transferred into the resultant bacterial strain *Corynebacterium glutamicum* ATCC13032 [pTET3, pEBM2], which bears the plasmids pTET3 and pEBM2. After DNA transfer, selection was performed on LB agar containing 7.5 µg/ml of chloramphenicol (Sigma-Aldrich Chemie GmbH, Deisenhofen, Germany). In order to confirm completion of the plasmid transfer, plasmid DNA was isolated from the resultant strains or transformants ("NucleoBond Nucleic Acid Purification Kits and Cartridges User Manual (PT3167-1)", Clonetech Laboratories GmbH, Heidelberg, Germany, 1997) and detected in 0.8% agarose gel.

In this manner, the following strains of *Corynebacterium glutamicum* were produced:

ATCC13032 [pTET3, pGA1-KE12]
ATCC13032 [pTET3, pAG3-Xba]
ATCC13032 [pTET3, pEBM2]
ATCC13032 [pTET3, pECM2]
ATCC13032 [pTET3, pEBM2, pECM3].

In order to provide further evidence of the coexistence of the novel plasmid pTET3 with known plasmid vectors, the strains produced were initially cultured for 24 hours at 30° C. in LB medium, which had been supplemented with the appropriate antibiotics (5 µg/ml of tetracycline, 25 µg/ml of kanamycin and 10 µg/ml of chloramphenicol). 1 ml portions of each of the cultures were then washed twice in antibiotic-free LB medium. Dilution series of the washed bacterial suspensions were prepared in LB medium and suspensions of 0.1 ml, which contained $10^4$ cells, were transferred in each case onto 100 ml of antibiotic-free and antibiotic-containing LB medium. These cultures were again cultured at 30° C. over approximately 25 generations and growth monitored by measuring optical density at a wavelength of 580 nm using a spectrophotometer (Pharmacia LKB Novaspec II, Pharmacia, Freiburg, Germany). The cultures were cultured at least up to an optical density of 8 (optical density of 1 corresponds to $4 \times 10^8$ cells per ml).

The plasmid DNA was then isolated from the cultures and separated in 0.8% agarose gel. The resultant plasmid bands were identical under both culture conditions, i.e. in the presence and absence of antibiotics, and each exhibited the presence of plasmid pTET3 and of the transformed plasmid vector, i.e. pGA1-KE12, pAG3-Xba, pEBM2, pECM2, and pEBM2 plus pECM3.

EXAMPLE 8

Coexistence of Plasmid pCRY4 with Other Coryneform Plasmids in *Corynebacterium glutamicum* LP-6

*Corynebacterium glutamicum* LP-6, in which pCRY4 already coexists with plasmids pGA1, pGA2 and pTET3, was used to analyse the coexistence of plasmid pCRY4 with known coryneform plasmids.

Further plasmid vectors consisting of known coryneform plasmids and selection marker fractions were transferred into this bacterial strain. Plasmid vectors pAG3-Xba, pEBM2 (Tauch et al., Archives of Microbiology 169, 303–312 (1998)), pECM2 (Tauch et al., FEMS Microbiology Letters 123, 343–348 (1994)) and pECM3 were used for this DNA transfer. Plasmid pECM3 is a BamHI-BglII deletion of pECM2. Transfer of the plasmid vectors pAG3-Xba (pAG3 derivative), pEBM2 (pBL1 derivatives) and pECM2 (pHM1519 derivative) was selected on LB agar containing 25 µg/ml of kanamycin. The plasmid pECM3, a pHM1519 derivative, which imparts chloramphenicol resistance was additionally transferred into the resultant bacterial strain *Corynebacterium glutamicum* LP-6 [pEBM2], which bears the plasmids pGA1, pGA2, pTET3, pCRY4 and pEBM2. After DNA transfer, selection was performed on LB agar containing 7.5 µg/ml of chloramphenicol. In order to confirm successful plasmid transfer, plasmid DNA was isolated from the resultant strains or transformants ("NucleoBond Nucleic Acid Purification Kits and Cartridges User Manual (PT3167-1)", Clonetech Laboratories GmbH, Heidelberg, Germany, 1997) and detected in 0.8% agarose gel.

In this manner, the following strains of *Corynebacterium glutamicum* were produced:

LP-6 [pAG3-Xba]

LP-6 [pEBM2]

LP-6 [pECM2]

LP-6 (pEBM2, pECM3].

(It should be noted that the recipient strain, *Corynebacterium glutamicum* LP-6, already contains plasmids pGA1, pGA2, pTET3 and pCRY4.)

In order to provide further evidence of the coexistence of the plasmid pCRY4 with known plasmid vectors, the strains produced were initially cultured for 24 hours at 30° C. in LB medium, which had been supplemented with the appropriate antibiotics (5 µg/ml of tetracycline, 25 µg/ml of kanamycin and 10 µg/ml of chloramphenicol). 1 ml portions of the bacterial cultures were then washed twice in antibiotic-free LB medium. Dilution series of the washed bacterial suspensions were prepared in LB medium and suspensions of 0.1 ml, which contained $10^4$ cells, were transferred in each case onto 100 ml of antibiotic-free and antibiotic-containing LB medium. These cultures were again cultured at 30° C. over approximately 25 generations and growth monitored by measuring optical density at a wavelength of 580 nm using a spectrophotometer (Pharmacia LKB Novaspec II, Pharmacia, Freiburg, Germany). The cultures were cultured at least up to an optical density of 8 (optical density of 1 corresponds to $4 \times 10^8$ cells per ml). The plasmid DNA was then isolated from the cultures and separated in 0.8% agarose gel. The resultant plasmid bands were identical under selective and non-selective culture conditions, i.e. in the presence and absence of antibiotics, and each exhibited the presence of plasmids pGA1, pGA2, pTET3 and pCRY4 and of the transformed plasmid vector, i.e. pAG3-Xba, pEBM2, pECM2 and pEBM2 plus pECM3.

EXAMPLE 9

Construction of Plasmid Vector pSELF3-1 from pTET3

Figure 6:
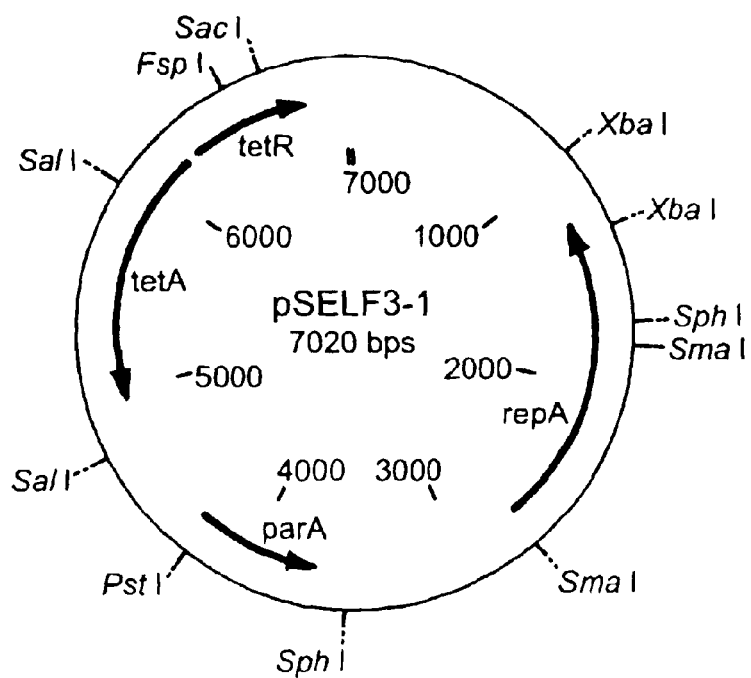
FIG. 6: Map of plasmid vector pSELF3-1.

In order to construct a plasmid vector consisting solely of components of the novel plasmid pTET3, the total plasmid DNA from *Corynebacterium glutamicum* LP-6 was isolated by alkaline treatment of the bacterial cells ("NucleoBond Nucleic Acid Purification Kits and Cartridges User Manual (PT3167-1)", Clonetech Laboratories GmbH, Heidelberg, Germany, 1997). The resultant DNA preparation was then separated in a 0.8% agarose gel. The plasmid band corresponding to the novel plasmid pTET3 was reisolated from the agarose gel ("QIAEX II Handbook for DNA Extraction from Agarose Gels", Qiagen GmbH, Hilden, Germany). The reisolated plasmid DNA was then digested with the restriction enzyme XhoI (Pharmacia Biotech Europe GmbH, Freiburg, Germany) in accordance with the manufacturer's instructions. The restriction batch was separated in a 0.8% agarose gel and an approximately 2500 bp DNA fragment, on which, according to DNA sequence data (Example 6), the tetracycline resistance region is located, was reisolated. The isolated pTET3 DNA was then cleaved with the restriction enzymes AvrII (New England Biolabs GmbH, Schwalbach, Germany) and HpaI (Pharmacia Biotech Europe GmbH, Freiburg, Germany). The cleavage batch was also separated in a 0.8% agarose gel and the approximately 4500 bp DNA fragment, on which, according to the DNA sequence information, the replication region of pTET3 is located, was reisolated. The projecting DNA ends of both the reisolated DNA fragments were then filled in with the enzyme Klenow polymerase. The fill-in reaction with the enzyme Klenow polymerase was performed in accordance with the manufacturer's instructions (Roche Diagnostics GmbH, Mannheim, Germany). The filled in DNA fragments were then ligated together by the enzyme T4 DNA ligase (Roche Diagnostics GmbH, Mannheim, Germany) in accordance with the manufacturer's instructions. The ligation mixture was transferred into *Corynebacterium glutamicum* ATCC13032 by electroporation. Selection was performed on LB agar containing 5 µg/ml of tetracycline. After 48 hours' incubation at 30° C., colonies were isolated which contain the novel plasmid vector. The presence of plasmid vector in the transformed bacterial cells was demonstrated using an alkaline lysis method ("QIAGEN Plasmid Mini Handbook for Plasmid Mini Kit", Qiagen GmbH, Hilden, Germany, 1997). The isolated plasmid was named pSELF3-1. Restriction analyses ills of pSELF3-1 and a comparison of the fragment lengths obtained with DNA fragments of known length yielded the restriction map in FIG. 6.

Due to this construction scheme, plasmid pSELF3-1 consists solely of DNA fragments of the novel plasmid pTET3 and thus of DNA which originates solely from *Corynebacterium glutamicum*.

EXAMPLE 10

Construction of Plasmid Vector pSELF1-1

Plasmid vector pSELF1-1 was produced from known plasmid pGA1 (U.S. Pat. No. 5,175,108) using the tetracycline resistance gene from pTET3 (c.f. Examples 1 and 6).

Figure 7:
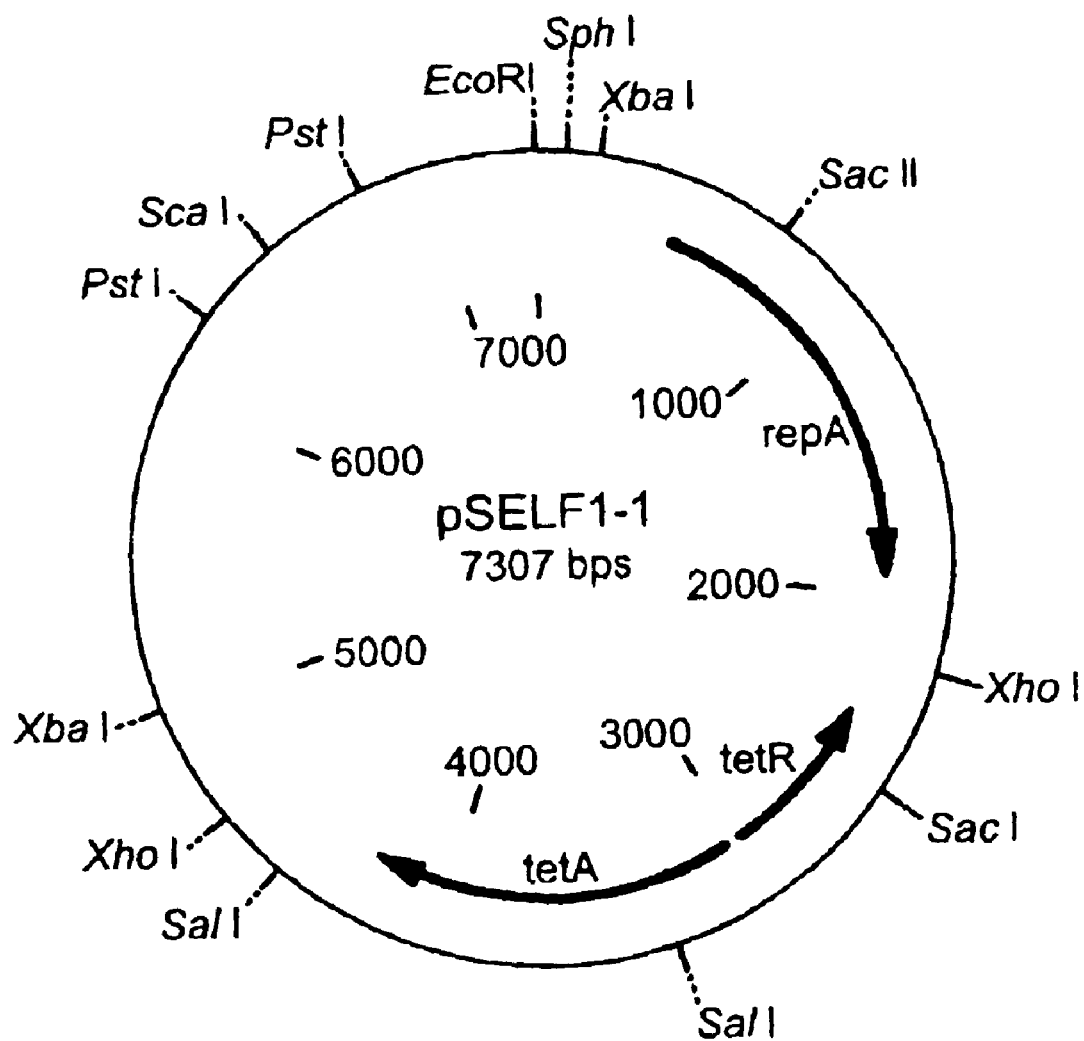
FIG. 7: Map of plasmid vector pSELF1-1.

To this end, the total plasmid DNA of *Corynebacterium glutamicum* LP-6 was initially isolated by alkaline treatment of the bacterial cells ("NucleoBond Nucleic Acid Purification Kits and Cartridges User Manual (PT1997-6)", Clonetech Laboratories GmbH, Heidelberg, Germany, 1997). The resultant DNA preparation was separated in a 0.8% agarose gel. The plasmid bands corresponding to the known plasmid pGA1 and the novel plasmid pTET3 were reisolated from the agarose gel ("QIAEX II Handbook for DNA Extraction from Agarose Gels", Qiagen GmbH, Hilden, Germany). The isolated DNA from pGA1 was then cleaved with the restriction enzyme SalI (Pharmacia Biotech Europe GmbH, Freiburg, Germany) in accordance with the manufacturer's instructions. The isolated plasmid DNA of pTET3 was cleaved with the restriction enzyme XhoI (Pharmacia Biotech Europe GmbH, Freiburg, Germany). The restriction batch of pTET3 was separated in a 0.8% agarose gel and an approximately 2500 bp DNA fragment, on which, according to DNA sequence data (Example 6), the tetracycline resistance region is located, was reisolated. The produced DNA fragment of pGA1 and the reisolated DNA fragment of pTET3 were then ligated together by means of T4 DNA ligase (Roche Diagnostics GmbH, Mannheim, Germany) in accordance with the manufacturer's instructions. The ligation mixture was transferred into *Corynebacterium glutamicum* ATCC13032 by electroporation. Selection was performed on LB agar containing 5 µg/ml of tetracycline. After 48 hours' incubation at 30° C., colonies were isolated which contained the novel plasmid vector. The presence of plasmid vector in the transformed bacterial cells was proven by an alkaline lysis method ("QIAGEN Plasmid Mini Handbook for Plasmid Mini Kit", Qiagen GmbH, Hilden, Germany, 1997). The isolated plasmid was named pSELF1-1. Restriction analyses of pSELF1-1 and a comparison of the fragment lengths obtained with DNA fragments of known length yielded the restriction map which is attached as FIG. 7.

Due to this construction method, plasmid pSELF1-1 consists solely of DNA fragments which originate solely from *Corynebacterium glutamicum*.

EXAMPLE 11

Production of Lysine Using pSELF1-1

In order to increase the copy number of a gene which is involved in the biosynthesis of amino acid lysine in coryneform bacteria, the lysC(FBR) gene from *Corynebacterium glutamicum* was selected. The lysC(FBR) gene encodes a form of the enzyme aspartate kinase which is resistant to the antimetabolite S-(2-aminoethyl)cysteine and was in cloned form on the plasmid vector pJC30 (Cremer et al., Applied and Environmental Microbiology 57, 1746–1752 (1991)).

In order to clone the lysC(FBR) gene into the plasmid vector pSELF1-1 described in Example 10, plasmid DNA of, pSELF1-1 and of pJC30 was cleaved with the restriction enzymes EcoRI and ScaI (Pharmacia Biotech Europe GmbH, Freiburg, Germany). The restriction batches were then ligated together with the enzyme T4 DNA ligase (Roche Diagnostics GmbH, Mannheim, Germany) and transformed into the bacterial strain *Corynebacterium glutamicum* ATCC13032. Selection was performed on LB agar containing 5 µg/ml of tetracycline. Plasmid DNA was reisolated from transformed colonies by an alkaline lysis method ("QIAGEN Plasmid Mini Handbook for Plasmid Mini Kit", Qiagen GmbH, Hilden, Germany, 1997). By restriction analysis of this plasmid DNA and comparison with DNA fragments of known length, the plasmid pSELF1-lysC was isolated, which consists of the plasmid vector pSELF1-1 and the lysC(FBR) gene region.

The plasmids pSELF-lysC and the control vector pSELF1-1 were transferred into the strain *Corynebacterium glutamicum* ATCC13032 by electroporation. Plasmid transfer was then proven by alkaline lysis and gel electrophoresis ("QIAGEN Plasmid Mini Handbook for Plasmid Mini Kit", Qiagen GmbH, Hilden, Germany, 1997). The strains ATCC13032 [pSELF1-1] and ATCC13032 [pSELF1-lysC] constructed in this manner were used for the production of lysine.

Both strains were initially cultured for 24 hours at 30° C. in 50 ml of Luria-Bertani medium containing 5 µg/ml of tetracycline. 1 ml portions of culture were then washed twice in mineral medium (Broer et al., Applied and Environmental Microbiology 59, 316–321 (1993)), transferred into 100 ml of mineral medium with 5 µg/ml of tetracycline and incubated for a further 24 hours at 30° C. 5 ml portions of culture supernatant were pelletised for 15 minutes at 13800×g and 4° C. and sterile-filtered with a Millex-GS filter unit (0.22 µm, Millipore S. A., Molsheim, France). Lysine was determined in the filtered culture supernatants by means of HPLC analysis using the method of Buntemeyer et al. (Cytotechnology 5, 57–67 (1991)). The resultant lysine concentrations after 24 hours' culturing are summarised in Table 2.

TABLE 2

Lysine concentration in culture supernatants of various strains of *Corynebacterium glutamicum*.

| Host | Plasmid | Lysine concentration (g/l) |
| --- | --- | --- |
| ATCC13032 | pSELF1-1 | 0.02 |
| ATCC13032 | pSELF1-lysC | 1.0 |

EXAMPLE 12

Production of Pantothenic Acid Using pSELF3-1

In order to increase the copy number of a gene which is involved in the biosynthesis of pantothenate in coryneform bacteria, the panD gene from *Corynebacterium glutamicum* ATCC13032 was selected. The panD gene encodes the enzyme L-aspartate α-decarboxylase and was in cloned form on the plasmid vector pND10 (Dusch et al., Applied and Environmental Microbiology 65, 1530–1539 (1999)).

In order to clone the panD gene into the novel plasmid vector pSELF3-1 described in Example 9, plasmid DNA of pSELF3-1 was cleaved with the restriction enzymes SacI (Pharmacia Biotech Europe GmbH, Freiburg, Germany) and BstZ17I (New England Biolabs GmbH, Schwalbach, Germany) and plasmid DNA of pND10 was cleaved with the restriction enzymes SacI and ScaI (Pharmacia Biotech Europe GmbH, Freiburg, Germany) in accordance with the manufacturer's instructions. The restriction batches were then ligated together with the enzyme T4 DNA ligase in accordance with the manufacturer's instructions (Roche Diagnostics GmbH, Mannheim, Germany) and transformed into the bacterial strain *Corynebacterium glutamicum* ATCC13032. Selection was performed on LB agar containing 5 µg/ml of tetracycline. Plasmid DNA was reisolated from the transformed colonies by alkaline lysis ("QIAGEN Plasmid Mini Handbook for Plasmid Mini Kit", Qiagen GmbH, Hilden, Germany, 1997). By restriction analysis of the isolated plasmid DNA and comparison with DNA fragments of known length (DNA Molecular Weight Marker X, Roche Diagnostics GmbH, Mannheim, Germany), the plasmid pSELF3-panD was isolated, which consists of the plasmid vector pSELF3-1 and the region of pND10 which encodes the panD gene.

In order to analyse pantothenate production in coryneform bacteria, the constructed plasmid vector pSELF3-panD and the control vector pSELF3-1 were transferred into strain ATCC13032ΔilvA (Sahm et al., Applied and Environmental Microbiology 65, 1973–1979 (1999)). The presence of the plasmids was then proven by alkaline lysis ("QIAGEN Plasmid Mini Handbook for Plasmid Mini Kit", Qiagen GmbH, Hilden, Germany, 1997). The strains ATCC13032ΔilvA [pSELF3-1] and ATCC13032ΔilvA [pSELF3-panD] constructed in this manner were used for the production of pantothenate.

The bacterial strains were initially cultured for 24 hours at 30° C. in 50 ml of Luria-Bertani medium containing 5 µg/ml of tetracycline. 1 ml portions of the bacterial culture were then washed twice with CGXII medium (Keilhauer et al., Journal of Bacteriology 175, 5595–5603, (1993)), to which 2 mM of isoleucine (Sigma-Aldrich Chemie GmbH, Deisenhofen, Germany) had been added, were transferred into 50 ml of CGXII medium with 2 mM of isoleucine and 5 µg/ml of tetracycline and cultured for 24 hours at 30° C. A further 50 ml of CGXII medium containing 2 mM of isoleucine were inoculated with 3 ml of this culture. After further incubation of the batch for 24 hours at 30° C., 20 ml of the bacterial culture were pelletised for 10 minutes at 1250×g. The culture supernatant was then sterile-filtered with a Millex-GS filter unit (0.22 μm, Millipore S. A., Molsheim, France). Pantothenate concentration was determined in the filtered culture supernatants in accordance with the instructions in the Difco Manual, 10th Edition (Difco Laboratories, Detroit, Mich., USA). The resultant pantothenate concentrations after 24 hours' culturing are summarised in Table 3.

TABLE 3

Pantothenate concentration in culture supernatants of various strains of *Corynebacterium glutamicum*.

| Host | Plasmid | Pantothenate concentration (ng/ml) |
|---|---|---|
| ATCC13032ΔilvA | pSELF3-1 | 14.1 |
| ATCC13032ΔilvA | pSELF3-panD | 54.1 |

The constructed plasmid vector pSELF3-panD was also used further to improve strain ATCC13032ΔilvA [pEKEx2panBC, pECM3ilvBNCD] (Sahm et al., Applied and Environmental Microbiology 65, 1973–1979 (1999)). This strain already bears the genes ilvBNCD and panBC, which have an advantageous effect on pantothenate biosynthesis, on known plasmid vectors.

Plasmid vector pSELF3-panD and the control vector pSELP3-1 were transferred by electroporation into strain ATCC13032ΔilvA [pEKEx2panBC, pECM3ilvENCD] (Sahm et al., Applied and Environmental Microbiology 65, 1973–1979 (1999)). Selection was performed on LB agar containing 5 μg/ml of tetracycline. The presence of the transferred plasmid vectors and the plasmids already present in the bacterial strain was then proven by alkaline lysis ("QIAGEN Plasmid Mini Handbook for Plasmid Mini Kit", Qiagen GmbH, Hilden, Germany, 1997). Both the strains constructed in this manner were also used in the manner described above for the production of pantothenate. The resultant pantothenate concentrations in the culture supernatants after 24 hours' culturing are shown in Table 4.

TABLE 4

Pantothenate concentration in culture supernatants of various strains of *Corynebacterium glutamicum*.

| Host | Plasmids | Pantothenate concentration (ng/ml) |
|---|---|---|
| ATCC13032ΔilvA | pECM3ilvBNCD pEKEx2panBC pSELF3-1 | 18.3 |
| ATCC13032ΔilvA | pECM3ilvBNCD pEKEx2panBC pSELF3-panD | 655.2 |

What is claimed is:

1. An isolated and purified plasmid capable of autonomous replication in bacteria of the genus Corynebacterium, said plasmid comprising:
   i) at least one region that encodes a protein involved in a biosynthetic pathway selected from the group consisting of L-lysine and pantothenic acid;
   ii) at least one DNA replication region obtained from one of the plasmids pTET3 or pCRY4, and
   iii) at least one region that encodes a protein for antibiotic resistance comprising a gene selected from the group consisting of a gene encoding a protein conferring tetracycline resistance, a gene encoding a protein conferring streptomycin and spectinomycin resistance, and a gene conferring sulfamethoxazole resistance, wherein said genes are obtained from the antibiotic resistance region of plasmid pTET3, as set forth in FIG. 5.

2. An isolated and purified plasmid capable of autonomous replication in bacteria of the genus Corynebacterium containing:
   i) at least one DNA replication region obtained from one of the plasmids pGA1, pGA2, pTET3 or pCRY4, and
   ii) at least one region which encodes a protein for antibiotic resistance comprising a gene selected from the group consisting of a gene encoding a protein conferring tetracycline resistance, a gene encoding a protein conferring streptomycin and spectinomycin resistance, and a gene conferring sulfamethoxazole resistance, wherein said genes are obtained from the antibiotic resistance region of plasmid pTET3, as set forth in FIG. 5.

3. The isolated and purified plasmid of claim 1 or 2, wherein said plasmid is capable of autonomous replication in bacteria of the species *Corynebacterium glutamicum*.

4. The isolated and purified plasmid of claim 2, wherein said plasmid consists of the DNA replication region obtained from pTET3 and at least one antibiotic resistance gene obtained from the antibiotic resistance gene region of plasmid pTET3, as set forth in FIG. 5.

5. Plasmid vector pELF3-1, which has a length of 7.0 kbp and the restriction map depicted in FIG. 6.

6. The plasmid of claim 2, wherein said plasmid comprises the DNA replication region of plasmid pGA1 and the tetA gene, imparting tetracycline resistance obtained from the antibiotic resistance region of plasmid pTET3.

7. Plasmid vector pSELF1-1, which has a length of ~7.3 kbp and the restriction map depicted in FIG. 7.

8. An isolated plasmid, designated pTET3, wherein said plasmid is characterized by:
   i) a length of ~27.8 kbp and the restriction map shown in FIG. 1,
   ii) a replication region comprising the nucleotide sequence shown in SEQ ID NO:1, and
   iii) an antibiotic resistance region, shown in FIG. 5, consisting of a tetA gene imparting tetracycline resistance, an aadA gene imparting streptomycin and spectinomycin resistance and a sulI gene imparting sulfamethoxazole resistance.

9. An isolated plasmid, designated pCRY4, wherein said is characterized by:
   i) a length of ~48 kbp and the restriction map shown in FIG. 2, and
   ii) a replication region comprising the nucleotide sequence shown in SEQ ID NO.4.

10. An isolated DNA sequence encoding at least one protein selected from the group consisting of:
    i) a protein comprising the amino acid sequence of SEQ ID NO:2, and
    ii) a protein comprising the amino acid sequence of SEQ ID NO:3.

11. An isolated DNA sequence comprising SEQ ID NO:1.

12. An isolated DNA sequence encoding a protein comprising the amino acid sequence of SEQ ID NO:5.

13. An isolated DNA comprising SEQ ID NO:4.

14. The plasmid of claim 1, wherein the region encoding a protein involved in a biosynthetic pathway consists of a lysC gene of *C. glutamicum* encoding an aspartate kinase and a panD gene of *C. glutamicum* encoding an aspartate α-decarboxylase.

* * * * *